(12) United States Patent
Alston et al.

(10) Patent No.: US 12,329,897 B2
(45) Date of Patent: Jun. 17, 2025

(54) VAPORIZER INCLUDING POSITIVE TEMPERATURE COEFFICIENT OF RESISTIVITY (PTCR) HEATING ELEMENT

(71) Applicant: JUUL Labs, Inc., San Francisco, CA (US)

(72) Inventors: William W. Alston, Lincoln, CA (US); Adam Bowen, San Mateo, CA (US); Joshua A. Kurzman, San Francisco, CA (US); James Monsees, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 345 days.

(21) Appl. No.: 17/875,697

(22) Filed: Jul. 28, 2022

(65) Prior Publication Data

US 2022/0370736 A1   Nov. 24, 2022

Related U.S. Application Data

(63) Continuation of application No. 16/566,842, filed on Sep. 10, 2019, now Pat. No. 11,413,409.
(Continued)

(51) Int. Cl.
  *A61M 11/04*   (2006.01)
(52) U.S. Cl.
  CPC ... *A61M 11/042* (2014.02); *A61M 2205/3368* (2013.01); *A61M 2205/8206* (2013.01)
(58) Field of Classification Search
  CPC .................................................... A24F 40/46
  See application file for complete search history.

(56) References Cited

U.S. PATENT DOCUMENTS

| | | |
|---|---|---|
| 4,735,217 A | 4/1988 | Gerth et al. |
| 4,947,875 A | 8/1990 | Brooks et al. |
| (Continued) | | |

FOREIGN PATENT DOCUMENTS

| | | |
|---|---|---|
| CA | 2935072 C | 8/2015 |
| CN | 1205849 C | 6/2005 |
| (Continued) | | |

OTHER PUBLICATIONS

Becker, et al. (Jul. 1, 1985) "PTC Heating Elements-Background Analysis and Design Attributes", 8095 IEEE Transactions on Industry, IA-21(4):896-898.
(Continued)

*Primary Examiner* — Truc T Nguyen
(74) *Attorney, Agent, or Firm* — Mintz, Levin, Cohn, Ferris, Glovsky and Popeo, P.C.

(57) ABSTRACT

An apparatus includes a housing including a power source; a reservoir including an inlet, an outlet, and configured to contain vaporizable material and couple to the housing; and a PTCR heating element configured to electrically couple to the power source and heat the vaporizable material to form an aerosol. The PTCR heating element includes an electrical resistivity that varies based on temperature. The electrical resistivity includes an electrical resistivity transition zone including an increase in electrical resistivity over a temperature range such that, when the PTCR heating element is heated to a first temperature within the transition zone, current flow from the power source is reduced to a level that limits further temperature increases of the PTCR heating element. Related apparatus, systems, techniques, and articles are also described.

17 Claims, 25 Drawing Sheets
(24 of 25 Drawing Sheet(s) Filed in Color)

Related U.S. Application Data

(60) Provisional application No. 62/897,229, filed on Sep. 6, 2019, provisional application No. 62/730,257, filed on Sep. 12, 2018.

(56) References Cited

U.S. PATENT DOCUMENTS

| | | | |
|---|---|---|---|
| 5,144,962 A | 9/1992 | Counts et al. | |
| 5,498,855 A * | 3/1996 | Deevi | A24F 40/46 131/194 |
| 5,819,756 A | 10/1998 | Mielordt | |
| 5,865,186 A | 2/1999 | Volsey, II | |
| 5,894,841 A | 4/1999 | Voges | |
| 6,155,268 A | 12/2000 | Takeuchi et al. | |
| 7,987,846 B2 | 8/2011 | Hale et al. | |
| 8,820,330 B2 | 9/2014 | Bellinger et al. | |
| 8,851,083 B2 | 10/2014 | Oglesby et al. | |
| 8,905,040 B2 | 12/2014 | Scatterday et al. | |
| 8,931,492 B2 | 1/2015 | Scatterday | |
| 8,991,402 B2 | 3/2015 | Bowen et al. | |
| 9,038,626 B2 | 5/2015 | Yamada et al. | |
| 9,095,175 B2 | 8/2015 | Terry et al. | |
| 9,101,729 B2 | 8/2015 | Liu et al. | |
| 9,132,248 B2 | 9/2015 | Qiu et al. | |
| 9,220,303 B2 | 12/2015 | Li et al. | |
| 9,282,772 B2 | 3/2016 | Tucker et al. | |
| 9,308,336 B2 | 4/2016 | Newton et al. | |
| 9,320,300 B2 | 4/2016 | Hon et al. | |
| 9,326,547 B2 | 5/2016 | Tucker et al. | |
| 9,364,800 B2 | 6/2016 | Dubief et al. | |
| 9,380,810 B2 | 7/2016 | Rose et al. | |
| 9,408,416 B2 | 8/2016 | Monsees et al. | |
| 9,440,035 B2 | 9/2016 | Chung et al. | |
| 9,456,633 B2 | 10/2016 | Liu et al. | |
| 9,474,306 B2 | 10/2016 | Tucker et al. | |
| 9,497,994 B2 | 11/2016 | Liu et al. | |
| 9,498,002 B1 | 11/2016 | Soreide et al. | |
| 9,498,588 B2 | 11/2016 | Benassayag et al. | |
| 9,510,623 B2 | 12/2016 | Tucker et al. | |
| 9,510,624 B2 | 12/2016 | Li et al. | |
| 9,532,604 B2 | 1/2017 | Conley et al. | |
| 9,555,203 B2 | 1/2017 | Terry et al. | |
| 9,623,205 B2 | 4/2017 | Buchberger | |
| 9,629,394 B2 | 4/2017 | Aronie et al. | |
| 9,668,523 B2 | 6/2017 | Tucker et al. | |
| 9,675,109 B2 | 6/2017 | Monsees et al. | |
| 9,675,113 B2 | 6/2017 | Liu et al. | |
| 9,675,117 B2 | 6/2017 | Li et al. | |
| 9,687,027 B2 | 6/2017 | Poston et al. | |
| 9,687,028 B2 | 6/2017 | Park et al. | |
| 9,714,878 B2 | 7/2017 | Powers et al. | |
| 9,717,276 B2 | 8/2017 | Brammer et al. | |
| 9,717,278 B2 | 8/2017 | Hon et al. | |
| 9,738,622 B2 | 8/2017 | Dull et al. | |
| 9,743,691 B2 | 8/2017 | Minskoff et al. | |
| 9,770,055 B2 | 9/2017 | Cameron et al. | |
| 9,802,011 B2 | 10/2017 | Davidson et al. | |
| 9,808,032 B2 | 11/2017 | Yamada et al. | |
| 9,814,263 B2 | 11/2017 | Cochand et al. | |
| 9,854,839 B2 | 1/2018 | Tucker et al. | |
| 9,877,511 B2 | 1/2018 | Li et al. | |
| 9,901,120 B2 | 2/2018 | Liu et al. | |
| 9,955,726 B2 | 5/2018 | Brinkley et al. | |
| 9,956,357 B2 | 5/2018 | Chen et al. | |
| 9,974,338 B2 | 5/2018 | Alarcon et al. | |
| 9,974,743 B2 | 5/2018 | Rose et al. | |
| 9,999,250 B2 | 6/2018 | Minskoff et al. | |
| 10,010,695 B2 | 7/2018 | Buchberger et al. | |
| 10,015,990 B2 | 7/2018 | Mironov et al. | |
| 10,021,912 B2 | 7/2018 | Yamada et al. | |
| 10,039,321 B2 | 8/2018 | Verleur et al. | |
| 10,045,562 B2 | 8/2018 | Buchberger et al. | |
| 10,045,564 B2 | 8/2018 | Hon et al. | |
| 10,064,434 B2 | 9/2018 | Zitzke et al. | |
| 10,085,481 B2 | 10/2018 | Verleur et al. | |
| 10,085,489 B2 | 10/2018 | Hon et al. | |
| 10,092,713 B2 | 10/2018 | Terry et al. | |
| 10,111,464 B1 | 10/2018 | Balder et al. | |
| 10,130,780 B2 | 11/2018 | Talon et al. | |
| 10,131,532 B2 | 11/2018 | Murison et al. | |
| 10,143,233 B2 | 12/2018 | Dubief et al. | |
| 10,159,278 B2 | 12/2018 | Minskoff et al. | |
| 10,159,282 B2 | 12/2018 | Monsees et al. | |
| 10,178,880 B2 | 1/2019 | Dubief et al. | |
| 10,188,148 B2 | 1/2019 | Althorpe et al. | |
| 10,194,693 B2 | 2/2019 | Wensley et al. | |
| 10,195,370 B2 | 2/2019 | Chen et al. | |
| 10,206,429 B2 | 2/2019 | Davis et al. | |
| 10,238,144 B2 | 3/2019 | Hon et al. | |
| 10,244,793 B2 | 4/2019 | Monsees et al. | |
| 10,278,421 B2 | 5/2019 | Lord et al. | |
| 10,278,427 B2 | 5/2019 | Buchberger | |
| 10,292,434 B2 | 5/2019 | Brinkley et al. | |
| 10,300,225 B2 | 5/2019 | Terry et al. | |
| 10,334,881 B1 | 7/2019 | Conley et al. | |
| 10,357,623 B2 | 7/2019 | Fang et al. | |
| 10,369,302 B2 | 8/2019 | Suzuki et al. | |
| 10,375,990 B2 | 8/2019 | Lord et al. | |
| 10,383,366 B2 | 8/2019 | Hon et al. | |
| 10,383,367 B2 | 8/2019 | Rasmussen et al. | |
| 10,398,176 B2 | 9/2019 | Hon et al. | |
| 10,405,579 B2 | 9/2019 | Collett et al. | |
| 10,405,583 B2 | 9/2019 | Tucker et al. | |
| 10,426,199 B2 | 10/2019 | Turner et al. | |
| 10,512,282 B2 | 12/2019 | Bowen et al. | |
| 10,517,331 B2 | 12/2019 | Atkins et al. | |
| 11,403,409 B2 | 8/2022 | Bradbury et al. | |
| 12,122,936 B2 * | 10/2024 | Fish | C09D 183/14 |
| 2002/0079309 A1 | 6/2002 | Cox et al. | |
| 2005/0016550 A1 | 1/2005 | Katase et al. | |
| 2013/0298905 A1 | 11/2013 | Levin et al. | |
| 2014/0261495 A1 | 9/2014 | Novak, III et al. | |
| 2015/0013695 A1 | 1/2015 | Mcneal et al. | |
| 2015/0090253 A1 | 4/2015 | Farrow et al. | |
| 2015/0201674 A1 | 7/2015 | Dooly et al. | |
| 2015/0257449 A1 | 9/2015 | Gabbay | |
| 2016/0021932 A1 | 1/2016 | Silvestrini et al. | |
| 2016/0205727 A1 | 7/2016 | Meinhart et al. | |
| 2016/0227838 A1 | 8/2016 | Johnson et al. | |
| 2016/0278163 A1 | 9/2016 | Chen et al. | |
| 2016/0286860 A1 | 10/2016 | Flayler et al. | |
| 2016/0309784 A1 | 10/2016 | Silvestrini et al. | |
| 2016/0309789 A1 | 10/2016 | Thomas et al. | |
| 2016/0316821 A1 | 11/2016 | Liu et al. | |
| 2016/0331023 A1 | 11/2016 | Cameron et al. | |
| 2016/0331034 A1 | 11/2016 | Cameron et al. | |
| 2016/0337362 A1 | 11/2016 | Cameron et al. | |
| 2016/0360786 A1 | 12/2016 | Bellinger et al. | |
| 2016/0366939 A1 | 12/2016 | Alarcon et al. | |
| 2017/0013880 A1 | 1/2017 | Brien et al. | |
| 2017/0014582 A1 | 1/2017 | Skoda et al. | |
| 2017/0020190 A1 | 1/2017 | Chang et al. | |
| 2017/0042245 A1 | 2/2017 | Buchberger et al. | |
| 2017/0045994 A1 | 2/2017 | Murison et al. | |
| 2017/0049149 A1 | 2/2017 | Carty et al. | |
| 2017/0049153 A1 | 2/2017 | Guo et al. | |
| 2017/0079321 A1 | 3/2017 | Golz et al. | |
| 2017/0099877 A1 | 4/2017 | Worm et al. | |
| 2017/0127727 A1 | 5/2017 | Davidson et al. | |
| 2017/0136193 A1 | 5/2017 | Cameron et al. | |
| 2017/0136194 A1 | 5/2017 | Cameron et al. | |
| 2017/0136196 A1 | 5/2017 | Davidson et al. | |
| 2017/0143917 A1 | 5/2017 | Cohen et al. | |
| 2017/0157341 A1 | 6/2017 | Pandya et al. | |
| 2017/0202266 A1 | 7/2017 | Sur et al. | |
| 2017/0231280 A1 | 8/2017 | Anton et al. | |
| 2017/0238605 A1 | 8/2017 | Matsumoto et al. | |
| 2017/0238608 A1 | 8/2017 | Matsumoto et al. | |
| 2017/0245550 A1 | 8/2017 | Freelander et al. | |
| 2017/0246405 A1 | 8/2017 | Wensley et al. | |
| 2017/0251726 A1 | 9/2017 | Nielsen et al. | |
| 2017/0266397 A1 | 9/2017 | Mayle et al. | |
| 2017/0273359 A1 | 9/2017 | Liu et al. | |
| 2017/0273914 A1 | 9/2017 | Knudsen et al. | |

(56) References Cited

U.S. PATENT DOCUMENTS

| | | |
|---|---|---|
| 2017/0281883 A1 | 10/2017 | Li et al. |
| 2017/0290369 A1 | 10/2017 | Norasak et al. |
| 2017/0290998 A1 | 10/2017 | Poston et al. |
| 2017/0295845 A1 | 10/2017 | Bajpai et al. |
| 2017/0318860 A1 | 11/2017 | Adair et al. |
| 2017/0325289 A1 | 11/2017 | Liu et al. |
| 2017/0325503 A1 | 11/2017 | Liu et al. |
| 2017/0325504 A1 | 11/2017 | Liu et al. |
| 2017/0333650 A1 | 11/2017 | Buchberger et al. |
| 2017/0354180 A1 | 12/2017 | Fornarelli et al. |
| 2017/0359858 A1 | 12/2017 | Liu et al. |
| 2017/0360094 A1 | 12/2017 | Kuczaj et al. |
| 2017/0367407 A1 | 12/2017 | Althorpe et al. |
| 2018/0007967 A1 | 1/2018 | Davis et al. |
| 2018/0020722 A1 | 1/2018 | Davis et al. |
| 2018/0020737 A1 | 1/2018 | Mironov et al. |
| 2018/0043114 A1 | 2/2018 | Bowen et al. |
| 2018/0043115 A1 | 2/2018 | Gould et al. |
| 2018/0070641 A1 | 3/2018 | Batista et al. |
| 2018/0077967 A1 | 3/2018 | Hatton et al. |
| 2018/0084831 A1 | 3/2018 | Mironov et al. |
| 2018/0110940 A1 | 4/2018 | Suzuki et al. |
| 2018/0117268 A1 | 5/2018 | Selby et al. |
| 2018/0162769 A1 | 6/2018 | Peuchert et al. |
| 2018/0184719 A1 | 7/2018 | Hon et al. |
| 2018/0184722 A1 | 7/2018 | Murison et al. |
| 2018/0199627 A1 | 7/2018 | Bowen et al. |
| 2018/0214645 A1 | 8/2018 | Reevell |
| 2018/0296777 A1 | 10/2018 | Terry et al. |
| 2018/0360116 A1 | 12/2018 | Schmidt et al. |
| 2019/0001077 A1 | 1/2019 | Xu et al. |
| 2019/0059444 A1 | 2/2019 | Cyphert et al. |
| 2019/0069599 A1 | 3/2019 | Monsees et al. |
| 2019/0124982 A1 | 5/2019 | Atkins et al. |
| 2019/0166913 A1 | 6/2019 | Trzecieski et al. |
| 2019/0191769 A1 | 6/2019 | Qiu |
| 2019/0387796 A1 | 12/2019 | Cohen et al. |
| 2020/0114094 A1 | 4/2020 | Atkins et al. |
| 2020/0120991 A1 | 4/2020 | Hatton et al. |
| 2020/0127475 A1 | 4/2020 | Cheung et al. |
| 2020/0146352 A1* | 5/2020 | Alston ............... A24F 40/46 |
| 2021/0337872 A1 | 11/2021 | Alston et al. |
| 2022/0279846 A1 | 9/2022 | Alston et al. |
| 2023/0054752 A1 | 2/2023 | Alston et al. |
| 2024/0306712 A1* | 9/2024 | Storz ................. H05B 3/46 |
| 2024/0349799 A1* | 10/2024 | Wang ............... A24F 40/40 |

FOREIGN PATENT DOCUMENTS

| | | |
|---|---|---|
| CN | 101862038 A | 10/2010 |
| CN | 204393344 U | 6/2015 |
| CN | 204409589 U | 6/2015 |
| CN | 105188429 A | 12/2015 |
| CN | 105815814 A | 8/2016 |
| CN | 105982363 A | 10/2016 |
| CN | 106455718 A | 2/2017 |
| CN | 107427080 A | 12/2017 |
| CN | 207476951 U | 6/2018 |
| CN | 109310157 A | 2/2019 |
| CN | 111213915 A | 6/2020 |
| EP | 0358114 A2 | 3/1990 |
| EP | 1412829 B1 | 4/2004 |
| EP | 2319334 A1 | 5/2011 |
| EP | 2606756 B1 | 6/2013 |
| EP | 2787848 A1 | 10/2014 |
| EP | 2797447 B1 | 11/2014 |
| EP | 2849590 B1 | 3/2015 |
| EP | 2925395 B1 | 10/2015 |
| EP | 2952110 A1 | 12/2015 |
| EP | 2967149 B1 | 1/2016 |
| EP | 2982255 B1 | 2/2016 |
| EP | 3000245 B1 | 3/2016 |
| EP | 3012213 A1 | 4/2016 |
| EP | 3019154 A1 | 5/2016 |
| EP | 3032975 B1 | 6/2016 |
| EP | 3038479 B1 | 7/2016 |
| EP | 3038686 B1 | 7/2016 |
| EP | 3081102 B1 | 10/2016 |
| EP | 3103356 B1 | 12/2016 |
| EP | 3104724 B1 | 12/2016 |
| EP | 3111787 A1 | 1/2017 |
| EP | 3117860 B1 | 1/2017 |
| EP | 3127437 B1 | 2/2017 |
| EP | 3138424 B1 | 3/2017 |
| EP | 3158883 B1 | 4/2017 |
| EP | 3214960 A1 | 9/2017 |
| EP | 3216359 A1 | 9/2017 |
| EP | 3292773 B1 | 3/2018 |
| EP | 3316711 B1 | 5/2018 |
| EP | 3331389 B1 | 6/2018 |
| GB | 1184656 A | 3/1970 |
| GB | 2468932 B | 9/2010 |
| GB | 2502164 B | 11/2013 |
| GB | 2550540 A | 11/2017 |
| GB | 2554141 B | 3/2018 |
| GB | 2568411 B | 5/2019 |
| JP | H06310261 A | 11/1994 |
| JP | H07183104 A | 7/1995 |
| JP | 2002124366 A | 4/2002 |
| JP | 2017515493 A | 6/2017 |
| JP | 2017519492 A | 7/2017 |
| JP | 2018536398 A | 12/2018 |
| JP | 2019513358 A | 5/2019 |
| KR | 20180127375 A | 11/2018 |
| TW | 201528979 A | 8/2015 |
| WO | WO-0028843 A1 | 5/2000 |
| WO | WO-2011109849 A1 | 9/2011 |
| WO | WO-2011125058 A1 | 10/2011 |
| WO | WO-2011160788 A1 | 12/2011 |
| WO | WO-2013030202 A1 | 3/2013 |
| WO | WO-2013060781 A1 | 5/2013 |
| WO | WO-2013083635 A1 | 6/2013 |
| WO | WO-2014095701 A1 | 6/2014 |
| WO | WO-2014125340 A1 | 8/2014 |
| WO | WO-2015079197 A1 | 6/2015 |
| WO | WO-2015114325 A1 | 8/2015 |
| WO | WO-2015137815 A1 | 9/2015 |
| WO | WO-2015138560 A1 | 9/2015 |
| WO | WO-2015189556 A1 | 12/2015 |
| WO | WO-2015193456 A1 | 12/2015 |
| WO | WO-2016020675 A1 | 2/2016 |
| WO | WO-2016030661 A1 | 3/2016 |
| WO | WO-2016071027 A1 | 5/2016 |
| WO | WO-2016122417 A1 | 8/2016 |
| WO | WO-2016135342 A2 | 9/2016 |
| WO | WO-2016145072 A1 | 9/2016 |
| WO | WO-2016179376 A1 | 11/2016 |
| WO | WO-2016200382 A1 | 12/2016 |
| WO | WO-2017001270 A1 | 1/2017 |
| WO | WO-2017021536 A2 | 2/2017 |
| WO | WO-2017033021 A1 | 3/2017 |
| WO | WO-2017033132 A1 | 3/2017 |
| WO | WO-2017046593 A2 | 3/2017 |
| WO | WO-2017051150 A1 | 3/2017 |
| WO | WO-2017055564 A1 | 4/2017 |
| WO | WO-2017055584 A1 | 4/2017 |
| WO | WO-2017055795 A1 | 4/2017 |
| WO | WO-2017055866 A1 | 4/2017 |
| WO | WO-2017102633 A1 | 6/2017 |
| WO | WO-2017108394 A1 | 6/2017 |
| WO | WO-2017122196 A1 | 7/2017 |
| WO | WO-2017163044 A1 | 9/2017 |
| WO | WO-2017163045 A1 | 9/2017 |
| WO | WO-2017163046 A1 | 9/2017 |
| WO | WO-2017163047 A1 | 9/2017 |
| WO | WO-2017163050 A1 | 9/2017 |
| WO | WO-2017176113 A1 | 10/2017 |
| WO | WO-2017207416 A1 | 12/2017 |
| WO | WO-2017207419 A1 | 12/2017 |
| WO | WO-2017207586 A1 | 12/2017 |
| WO | WO-2017214517 A1 | 12/2017 |
| WO | WO-2018010916 A1 | 1/2018 |
| WO | WO-2018019485 A1 | 2/2018 |
| WO | WO-2018027189 A2 | 2/2018 |

(56) References Cited

FOREIGN PATENT DOCUMENTS

| WO | WO-2018111879 A1 | 6/2018 |
| WO | WO-2018112178 A1 | 6/2018 |
| WO | WO-2018130391 A1 | 7/2018 |
| WO | WO-2018197515 A1 | 11/2018 |
| WO | WO-2018217926 A1 | 11/2018 |
| WO | WO-2019104223 A1 | 5/2019 |
| WO | WO-2020006148 A1 | 1/2020 |
| WO | WO-2020006305 A1 | 1/2020 |
| WO | WO-2020020788 A1 | 1/2020 |
| WO | WO-2020023535 A1 | 1/2020 |
| WO | WO-2020023540 A1 | 1/2020 |
| WO | WO-2020028591 A1 | 2/2020 |
| WO | WO-2020097567 A1 | 5/2020 |

OTHER PUBLICATIONS

Yan, Dawei, (May 31, 1994) "New 600 Questions and Answers on Computer and Electronic Technology, the First Edition", Weapon Industry Press, 299-300.

Jiang, et al. (Jul. 31, 2008) "Development of High-Performance PTCR Heating Elements for New Heaters", Device Manufacturing and Application, 33(7):600-602, 625.

\* cited by examiner

| Temperature (°C) | Resistivity (ohm-cm) | Temperature (°C) | Resistivity (ohm-cm) | Temperature (°C) | Resistivity (ohm-cm) |
|---|---|---|---|---|---|
| 22.3 | 109.694 | 184.2 | 38.685 | 232.3 | 162.394 |
| 23.6 | 108.330 | 184.7 | 38.673 | 233.2 | 256.665 |
| 33.5 | 98.611 | 187.0 | 38.625 | 233.8 | 331.375 |
| 38.5 | 94.008 | 188.0 | 38.607 | 234.8 | 441.487 |
| 46.9 | 86.630 | 190.0 | 38.578 | 235.6 | 558.977 |
| 47.1 | 86.506 | 190.2 | 38.576 | 236.3 | 678.110 |
| 52.2 | 82.600 | 192.0 | 38.556 | 236.5 | 711.822 |
| 59.5 | 77.991 | 193.0 | 38.547 | 238.3 | 1261.390 |
| 59.8 | 77.795 | 194.0 | 38.541 | 240.8 | 2687.390 |
| 64.8 | 74.769 | 195.6 | 38.532 | 240.9 | 2778.690 |
| 75.2 | 68.082 | 195.8 | 38.532 | 243.9 | 4442.150 |
| 77.7 | 66.681 | 197.3 | 38.527 | 244.2 | 4788.260 |
| 86.5 | 62.716 | 198.6 | 38.527 | 245.2 | 6747.000 |
| 86.6 | 62.653 | 199.1 | 38.528 | 247.1 | 9698.350 |
| 91.1 | 60.966 | 200.6 | 38.535 | 247.9 | 11432.800 |
| 99.4 | 57.955 | 201.2 | 38.538 | 250.7 | 22831.500 |
| 99.9 | 57.775 | 202.2 | 38.547 | 251.7 | 28992.800 |
| 104.7 | 56.019 | 203.1 | 38.556 | 252.5 | 34334.100 |
| 111.4 | 53.450 | 203.9 | 38.570 | 254.5 | 45742.100 |
| 116.9 | 51.472 | 204.5 | 38.583 | 254.8 | 47918.300 |
| 119.0 | 50.738 | 205.9 | 38.620 | 257.3 | 68258.900 |
| 122.5 | 49.605 | 207.7 | 38.711 | 260.8 | 111647.000 |
| 127.5 | 48.097 | 207.9 | 38.722 | 262.1 | 133176.000 |
| 133.9 | 46.362 | 209.0 | 38.831 | 262.8 | 143871.000 |
| 134.9 | 46.125 | 210.7 | 39.097 | 263.3 | 150490.000 |
| 139.4 | 45.173 | 211.7 | 39.351 | 265.1 | 170423.000 |
| 144.3 | 44.277 | 212.7 | 39.692 | 268.9 | 221852.000 |
| 147.3 | 43.769 | 213.6 | 40.122 | 271.4 | 256649.000 |
| 149.1 | 43.456 | 214.3 | 40.449 | 272.2 | 265081.000 |
| 151.8 | 42.994 | 215.6 | 41.185 | 272.5 | 268026.000 |
| 158.1 | 41.887 | 217.6 | 42.459 | 276.8 | 295802.000 |
| 159.1 | 41.714 | 219.3 | 43.660 | 278.5 | 303521.000 |
| 163.5 | 40.937 | 219.4 | 43.788 | 282.3 | 316247.000 |
| 165.2 | 40.655 | 220.8 | 44.857 | 285.1 | 322183.000 |
| 168.3 | 40.128 | 221.4 | 45.434 | 291.0 | 326120.000 |
| 168.8 | 40.046 | 222.4 | 46.404 | 292.2 | 324601.000 |
| 171.6 | 39.604 | 222.9 | 47.021 | 293.4 | 322183.000 |
| 174.1 | 39.274 | 224.4 | 50.439 | 297.5 | 307629.000 |
| 175.3 | 39.148 | 225.6 | 54.008 | 302.3 | 285898.000 |
| 178.1 | 38.925 | 227.2 | 60.796 | 303.8 | 279388.000 |
| 179.2 | 38.862 | 228.0 | 66.314 | 307.4 | 260106.000 |
| 180.1 | 38.821 | 228.4 | 70.170 | 310.1 | 239863.000 |
| 181.9 | 38.752 | 229.4 | 97.759 | 313.2 | 215295.000 |
| 182.1 | 38.747 | 231.0 | 129.069 | 315.2 | 200942.000 |

FIG. 1C

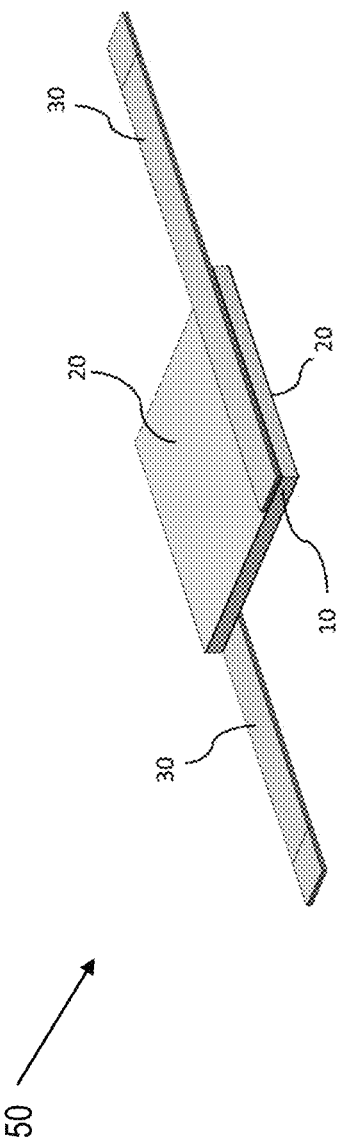
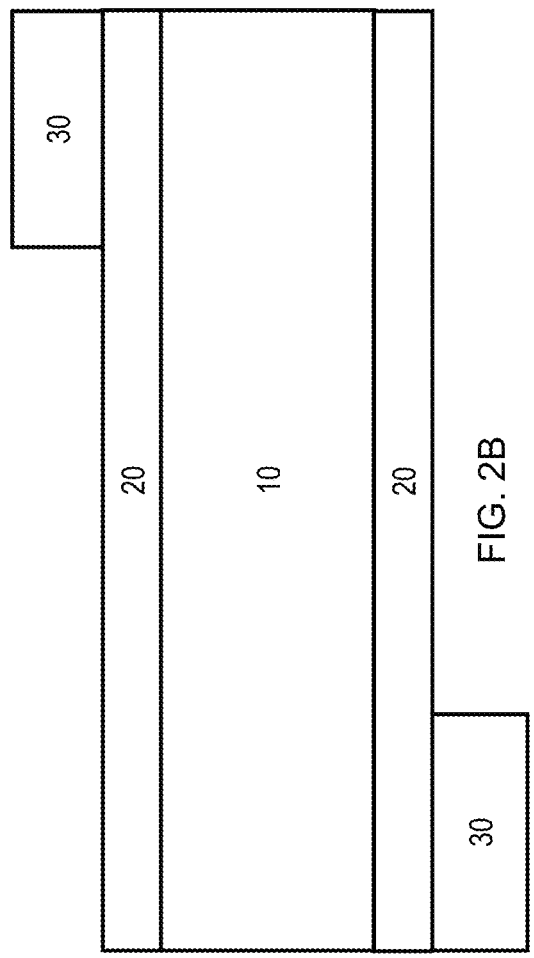

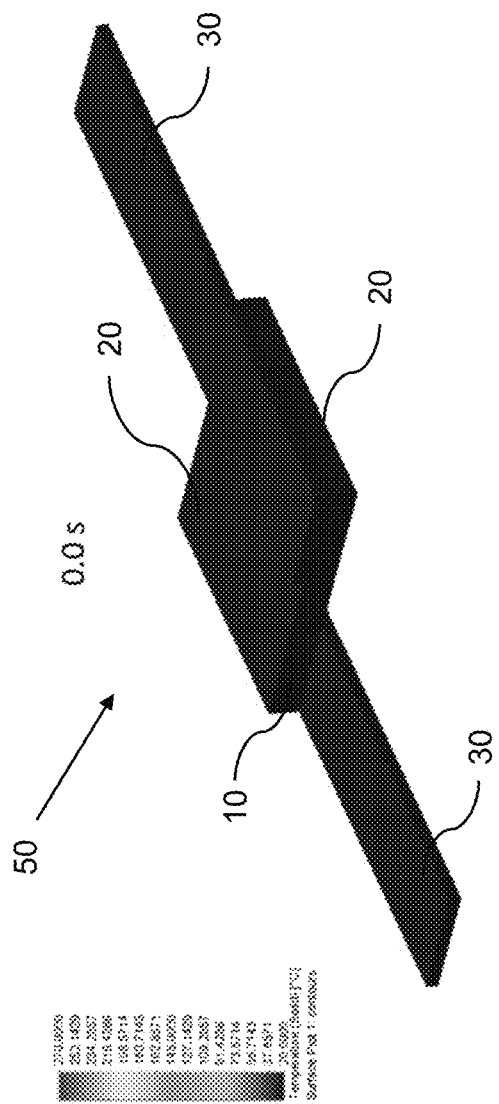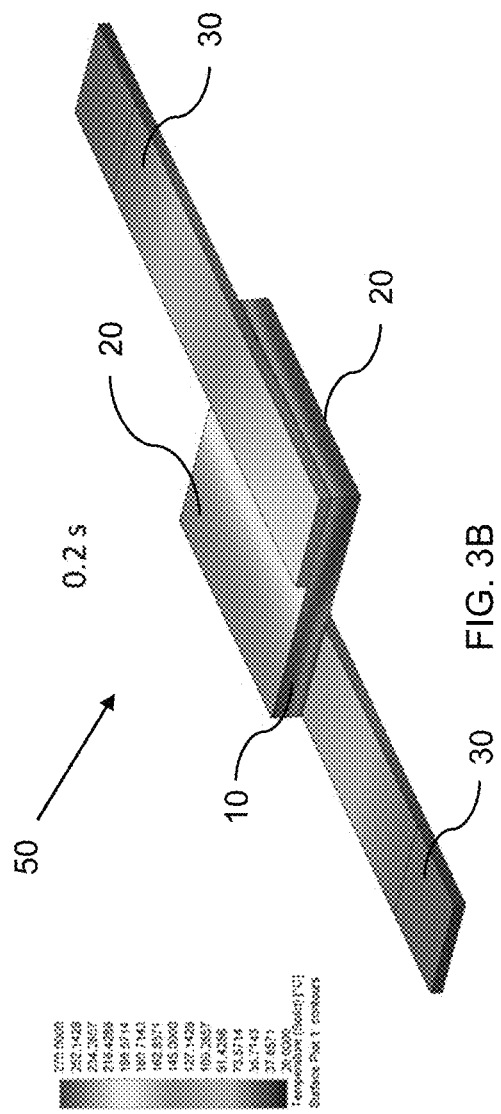

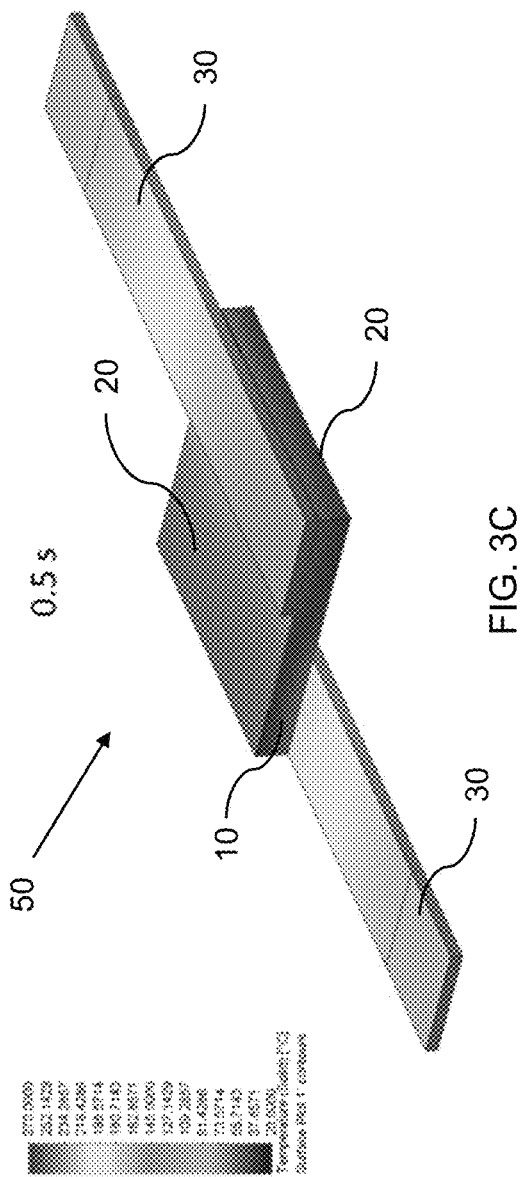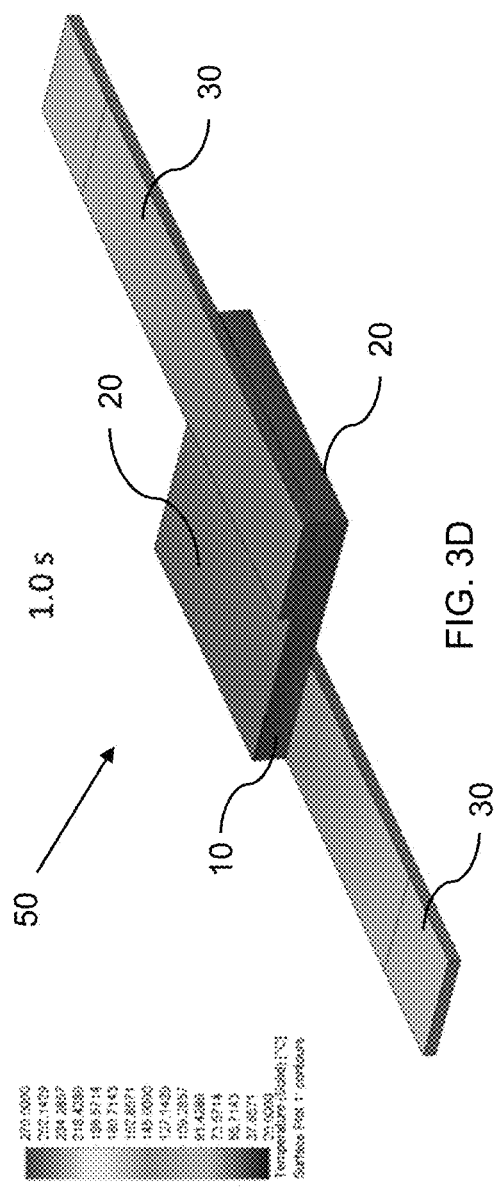
FIG. 3C
FIG. 3D

VAPORIZER INCLUDING POSITIVE TEMPERATURE COEFFICIENT OF RESISTIVITY (PTCR) HEATING ELEMENT

CROSS REFERENCE

The present application is a continuation of U.S. patent application Ser. No. 16/566,842 entitled "Vaporizer Including Positive Temperature Coefficient of Resistivity (PTCR) Heating Element filed on Sep. 10, 2019, which claims priority to U.S. Provisional Patent Application No. 62/730,257 entitled "Vaporizer Including Positive Temperature Coefficient of Resistivity Heater" filed on Sep. 12, 2018, and claims priority to U.S. Provisional Patent Application No. 62/897,229 entitled "Vaporizer Including (PTCR) Positive Temperature Coefficient of Resistivity Heating Element" filed on Sep. 6, 2019, each of which is hereby incorporated by reference in its entirety.

TECHNICAL FIELD

The subject matter described herein relates to vaporizer devices, such as portable personal vaporizer devices for generating an inhalable aerosol from one or more vaporizable materials and including a PTCR heating element utilizing semiconductive material with nonlinear positive temperature coefficient of resistivity.

BACKGROUND

Vaporizer devices, which can also be referred to as vaporizers, electronic vaporizer devices, or e-vaporizer devices, can be used for delivery of an aerosol (e.g., vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that may be used to simulate the experience of smoking, but without burning of tobacco or other substances. Vaporizers are gaining increasing popularity both for prescriptive medical use, in delivering medicaments, and for consumption of tobacco, nicotine, and other plant-based materials. Vaporizer devices may be portable, self-contained, and/or convenient for use.

In use of a vaporizer device, the user inhales an aerosol, colloquially referred to as "vapor," which may be generated by a PTCR heating element that vaporizes (e.g., causes a liquid or solid to at least partially transition to the gas phase) a vaporizable material, which may be liquid, a solution, a solid, a paste, a wax, and/or any other form compatible for use with a specific vaporizer device. The vaporizable material used with a vaporizer can be provided within a cartridge (e.g., a separable part of the vaporizer device that contains vaporizable material) that includes an inlet and an outlet (e.g., a mouthpiece) for inhalation of the aerosol by a user.

To receive the inhalable aerosol generated by a vaporizer device, a user may, in certain examples, activate the vaporizer device by taking a puff, which is detected by a pressure sensor that turns on a PTCR heating element, and/or by some other approach, such as a simple user-operated push-button switch. A puff as used herein can refer to inhalation by the user in a manner that causes a volume of air to be drawn into the vaporizer device such that the inhalable aerosol is generated by a combination of vaporized vaporizable material with the volume of air.

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (e.g., conductive, convective, and/or radiative) causes heating of a vaporizable material to produce a mixture of air and vaporized material to form a vapor for inhalation of the vaporizable material by a user of the vaporization device.

Certain components of the gas-phase vaporizable material may condense after being vaporized due to cooling and/or changes in pressure to thereby form an aerosol that includes particles of a condensed phase (e.g., liquid and/or solid) suspended in at least some of the air drawn into the vaporizer device via the puff. If the vaporizable material includes a semi-volatile compound (e.g., a compound such as nicotine, which has a relatively low vapor pressure under inhalation temperatures and pressures), the inhalable aerosol may include that semi-volatile compound in some local equilibrium between the gas and condensed phases.

Typically, the vaporizable material can be drawn out of a reservoir and into the vaporization chamber via a wicking element (e.g., a wick). Drawing of the vaporizable material into the vaporization chamber may be at least partially due to capillary action provided by the wick as the wick pulls the vaporizable material along the wick in the direction of the vaporization chamber. However, as vaporizable material is drawn out of the reservoir, the pressure inside the reservoir is reduced, thereby creating a vacuum and acting against the capillary action. This can reduce the effectiveness of the wick to draw the vaporizable material into the vaporization chamber, thereby reducing the effectiveness of the vaporization device to vaporize a desired amount of vaporizable material. Furthermore, the vacuum created in the reservoir can ultimately result in the inability to draw all of the vaporizable material into the vaporization chamber, thereby wasting vaporizable material. As such, improved vaporizer devices and/or vaporizer cartridges that improve upon or overcome these issues is desired.

Vaporizer devices can be controlled by one or more controllers, electronic circuits (e.g., sensors, heating elements), and/or the like on the vaporizer. Vaporizer devices may also wirelessly communicate with an external controller (e.g., a computing device such as a smartphone).

SUMMARY

In certain aspects of the current subject matter, challenges associated with heating devices for vaporizers may be addressed by inclusion of one or more of the features described herein or comparable/equivalent approaches as would be understood by one of ordinary skill in the art. Aspects of the current subject matter relate to methods and system for utilizing a PTCR (positive temperature coefficient of resistivity) heating element, also called a PTCR heater, characterized by an electrical resistivity that varies based on temperature in a vaporizer device.

In some implementations, an apparatus includes a power source configured to provide a current flow at a voltage; a reservoir configured to contain a vaporizable material; and a PTCR (positive temperature coefficient of resistivity) heating element configured to electrically couple to the power source to receive the current flow and heat the vaporizable material to form an aerosol. The PTCR heating element includes a PTCR material having an electrical resistivity that varies based on temperature. The electrical resistivity includes an electrical resistivity transition zone in which the electrical resistivity increases over a temperature range, such that when the PTCR heating element is heated above a first temperature within the transition zone, current flow from the power source is reduced to a level that limits further temperature increases of the PTCR heating element.

In some implementations, an apparatus includes a power source configured to provide a current flow at a voltage; a reservoir configured to contain a vaporizable material; and an atomizer coupled to the reservoir to receive the vaporizable material. The atomizer includes a PTCR (positive temperature coefficient of resistivity) heating element configured to electrically couple and receive current flow from the power source to vaporize the vaporizable material. The PTCR heating element is configured to heat to an operating temperature at which a resistivity reduces the current flow to prevent an increase in the operating temperature.

In some implementations, an apparatus includes a power source configured to provide a current flow at a voltage; a receptacle configured to receive a vaporizable material; and a PTCR (positive temperature coefficient of resistivity) heating element configured to electrically couple and receive current flow from the power source to vaporize the vaporizable material. The PTCR heating element configured to heat to an operating temperature at which a resistivity reduces the current flow to prevent an increase in the operating temperature.

In some implementations, an apparatus includes a power source configured to provide a current flow at a voltage; a receptacle configured to receive a vaporizable material; and a PTCR (positive temperature coefficient of resistivity) heating element configured to electrically couple and receive current flow from the power source to vaporize the vaporizable material. The PTCR heating element has a first resistivity of between 10 ohm-cm and 100 ohm-cm at 100° C. and a second resistivity of between 50000 ohm-cm and 150000 ohm-cm at 260° C.

In some variations, one or more of the following features may optionally be included in any feasible combination. In an aspect, an apparatus includes a housing including a power source; a fluid reservoir including an inlet, an outlet, and configured to contain fluid and couple to the housing; and a PTCR heating element configured to electrically couple to the power source and heat the fluid to form an aerosol. The PTCR heating element includes an electrical resistivity that varies based on temperature. The electrical resistivity includes an electrical resistivity transition zone including an increase in electrical resistivity over a temperature range, such that when the PTCR heating element is heated to a first temperature within the transition zone, current flow from the power source is reduced to a level that limits further temperature increases of the PTCR heating element from current flow.

One or more of the following features can be included in any feasible combination. For example, the PTCR heating element can be arranged between the inlet and the outlet. The apparatus can include a cartridge including the fluid reservoir, fluid within the fluid reservoir, the PTCR heating element, a wick configured to transport the fluid to a location for vaporization, and electrical contacts electrically coupled to the PTCR heating element and configured to provide electric current to the PTCR heating element from the power source. The PTCR heating element can be configured to heat the fluid at the location.

The apparatus can include an input configured to electrically connect the power source to the PTCR heating element in response to user input. The input can include a pushbutton. The PTCR heating element of the apparatus is self-regulating to maintain a predetermined temperature when activated. The apparatus does not require a pressure sensor, and/or a controller coupled to the pressure sensor to electrically connect the power source to the PTCR heating element and regulate a temperature thereof.

The electrical resistivity transition zone can begin at a first temperature of between 150° C. and 350° C. The electrical resistivity transition zone can begin at a first temperature of between 220° C. and 300° C. The electrical resistivity transition zone can begin at a first temperature between 240° C. and 280° C.

The increase in the electrical resistivity over the temperature range of the electrical resistivity transition zone can include an increase factor of at least 10, the increase factor characterizing a relative change in electrical resistivity between electrical resistivity at a first temperature associated with a start of the electrical resistivity transition zone and electrical resistivity at a second temperature associated with an end of the electrical resistivity transition zone. The increase in the electrical resistivity over the temperature range of the electrical resistivity transition zone can include an increase factor of at least 100, the increase factor characterizing a relative change in electrical resistivity between electrical resistivity at a first temperature associated with a start of the electrical resistivity transition zone and electrical resistivity at a second temperature associated with an end of the electrical resistivity transition zone. The increase in the electrical resistivity over the temperature range of the electrical resistivity transition zone can include an increase factor of at least 1000, the increase factor characterizing a relative change in electrical resistivity between electrical resistivity at a first temperature associated with a start of the electrical resistivity transition zone and electrical resistivity at a second temperature associated with an end of the electrical resistivity transition zone.

The electrical resistivity transition zone can begin at a first temperature and end at a second temperature. A difference between the first temperature and the second temperature can be 500° C. or less. A difference between the first temperature and the second temperature can be 200° C. or less. A difference between the first temperature and the second temperature can be 100° C. or less. A difference between the first temperature and the second temperature can be 50° C. or less.

The electrical resistivity transition zone can begin at a first temperature and the electrical resistivity of the PTCR heating element at temperatures below the first temperature can be between 20 ohm-cm and 200 ohm-cm. Ohm-cm and ohm-m are units of the electrical resistivity of a PTCR material and is directly proportional to its resistance and area of its cross section and inversely proportional to its length. The electrical resistivity of the PTCR heating element at temperatures below the first temperature can be between 2.0 ohm-cm and 20 ohm-cm. The electrical resistivity of the PTCR heating element at temperatures below the first temperature can be between 0.2 ohm-cm and 2.0 ohm-cm.

The increase in the electrical resistivity over the temperature range of the electrical resistivity transition zone includes an increase factor of at least 100, the increase factor characterizing a relative change in electrical resistivity between electrical resistivity at a first temperature associated with a start of the electrical resistivity transition zone and electrical resistivity at a second temperature associated with an end of the electrical resistivity transition zone. The first temperature can be between 200° C. and 350° C., a difference between the first temperature and the second temperature can be 200° C. or less, and the electrical resistivity of the PTCR heating element at temperatures below the first temperature can be between 20 ohm-cm and 200 ohm-cm.

The PTCR heating element can include a plate geometry including a height, a width, and a length; a polygon geometry; and/or a circle geometry. When the PTCR heating element includes a plate geometry, the height can be 0.5 mm, the length can be 5.0 mm, and the width can be 5.0 mm. The plate geometry can include two parallel sides with conductive leads attached thereto.

The PTCR heating element can include a positive temperature coefficient of resistivity material layer between a first electrically conductive layer and a second electrically conductive layer, the first electrically conductive layer coupled to a first conductive lead, the second electrically conductive layer coupled to a second conductive lead. The PTCR heating element can include a hole feature extending through the PTCR heating element. The PTCR heating element can include an aspect ratio of between 1 and 50.

The PTCR heating element can include a composition including a ceramic; a mixed-metal oxide; two or more mixed-metal oxides; a composite mixture of one or more mixed-metal oxides with one or more elemental metals, one or more binary metal oxides with MOx-type phases, one or more binary metal nitrides with MNx-type phases, with one or more binary metal carbides with MCx-type phases, with one or more binary metal borides with MBx-type phases, and/or with one or more binary metal silicides with MSix-type phases; a composite mixture of two or more binary metal oxides; a composite mixture of two or more binary metal oxides with one or more elemental metals, with one or more binary metal nitrides, with one or more binary metal carbides, with one or more binary metal borides, and/or with one or more binary metal silicides; and/or a cross-linked polymer composite with one or more elemental metals, with one or more binary metal oxides, with one or more binary metal nitrides, with one or more binary metal carbides, with one or more binary metal borides, and/or with one or more binary metal silicides; and/or any combination thereof.

The PTCR heating element can include a composition that can include $ABO_3$-type compounds where the identity of A includes Li, Na, K, Rb, Mg, Ca, Sr, Ba, Y, La, Ce, Pb, Bi, or mixtures thereof, and the identity of B includes Mg, Al, Sc, Ti, V, Cr, Mn, Fe, Co, Ni, Cu, Zn, Zr, Nb, Hf, Ta, or mixtures thereof; barium titanate ($BaTiO_3$); lead titanate ($PbTiO_3$); lead zirconate ($PbZrO_3$); bismuth aluminate ($BiAlO_3$); alkali niobates ($ANbO_3$, A=Li, Na, K, Rb), alkali tantalates ($ATaO_3$, A=Li, Na, K, Rb), or solid solutions thereof; solid solutions including main-group alkali zirconates ($Bi_{0.5}A_{0.5}ZrO_3$, A=Li, Na, K); solid solutions including main-group titanate-zirconates ($PbTi_{1-x}Zr_xO_3$), rare-earth substituted variants, and/or $Ba_{1-x}RE_xTiO_3$ (RE=La, Ce); alkaline earth niobates ($Sr_{1-x}Ba_xNb_2O_6$), Aurivillius-type phases of the general formula $[Bi_2O_2][A_{n-1}BnO_{3n+1}]$, $Bi_4Ti_3O_{12}$, substituted, solid solution, non-stoichiometric, and intergrowth phases thereof; elemental metals including C, Al, Si, Ti, Fe, Zn, Ag, and/or Bi; binary metal oxides including MgO, $Al_2O_3$, $SiO_2$, $TiO_2$, $Ti_2O_3$, $Cr_2O_3$, MnO, FeO, CoO, NiO, CuO, ZnO, and/or $SnO_2$; binary metal nitrides including TiN, $Mn_3N_2$, $Co_2N$, $Ni_3N$, and/or $Zn_3N_2$, binary metal carbides including TiC; binary metal borides including $ZrB_2$, and/or $NbB_2$; binary metal silicides including $NbSi_2$, $WSi_2$, and/or $MoSi_2$; polyethylene; polyamide; kynar; polytetrafluoroethylene; and/or any combination thereof.

The PTCR heating element can include a composition that can include $ABO_3$-type compounds where the identity of A includes Li, Na, K, Rb, Mg, Ca, Sr, Ba, Y, La, Ce, Pb, Bi, or mixtures thereof, and the identity of B includes Mg, Al, Sc, Ti, V, Cr, Mn, Fe, Co, Ni, Cu, Zn, Zr, Nb, Hf, Ta, or mixtures thereof. Examples of such compounds include: barium titanate ($BaTiO_3$), lead titanate ($PbTiO_3$), lead zirconate ($PbZrO_3$), bismuth aluminate ($BiAlO_3$), alkali niobates ($ANbO_3$, A=Li, Na, K, Rb), alkali tantalates ($ATaO_3$, A=Li, Na, K, Rb), or solid solutions thereof, such as main-group alkali zirconates ($Bi_{0.5}A_{0.5}ZrO_3$, A=Li, Na, K), titanate-zirconates ($PbTi_{1-x}Zr_xO_3$), and rare-earth substituted variants $Ba_{1-x}RE_xTiO_3$ (RE=La, Ce). Additionally or alternatively, compounds such as alkaline earth niobates ($Sr_{1-x}Ba_xNb_2O_6$), Aurivillius-type phases of the general formula $[Bi_2O_2] [A_{n-1}BnO_{3n+1}]$, or $Bi_4Ti_3O_{12}$ may be included or used. The compounds may be non-stoichiometric or intergrowth phases and are not constrained by nominal stoichiometry. The composition can include elemental metals including C, Al, Si, Ti, Fe, Zn, Ag, and/or Bi; binary metal oxides including MgO, $Al_2O_3$, $SiO_2$, $TiO_2$, $Ti_2O_3$, $Cr_2O_3$, MnO, FeO, CoO, NiO, CuO, ZnO, and/or $SnO_2$; binary metal nitrides including TiN, $Mn_3N_2$, $Co_2N$, $Ni_3N$, and/or $Zn_3N_2$, binary metal carbides including TiC; binary metal borides including $ZrB_2$, and/or $NbB_2$; binary metal silicides including $NbSi_2$, $WSi_2$, and/or $MoSi_2$; polymers including polyethylene; polyamide; kynar; and/or polytetrafluoroethylene.

The apparatus can include a wick adjacent the PTCR heating element, the wick configured to transport the fluid to a location for vaporization. The PTCR heating element can be configured to heat the fluid at the location for vaporization. The apparatus can include a second heating element, the second heating element adjacent a second side of the wick and the first heating element adjacent a first side of the wick. The wick can include an open weave configuration. The open weave configuration can be adjacent the first heating element, the second heating element, and/or cylindrical ends of the wick.

The power source can be configured to provide a voltage between 3 volts and 6 volts. In some implementations, the power source can be a battery, such as a rechargeable battery. In some implementations, the power source can provide a voltage between 3 to 10 volts, 3 to 50 volts, or 3 to 100 volts, among others. The power source can provide either direct current (DC) or alternating current (AC).

A method can include receiving, by a vaporizer apparatus, a user input, heating, using a PTCR heating element of the vaporizer apparatus, a vaporizable fluid, the PTCR heating element configured to electrically couple to a power source and heat the vaporizable fluid to form an aerosol. The PTCR heating element includes an electrical resistivity that varies based on temperature, the electrical resistivity including an electrical resistivity transition zone including an increase in electrical resistivity over a temperature range such that, when the PTCR heating element is heated to a first temperature within the transition zone, current flow from the power source is reduced to a level that limits further temperature increases of the PTCR heating element from current flow. The method can further include producing vapor by the heating of the vaporizable fluid.

In some implementations, an apparatus includes a housing including a power source; a fluid reservoir including an inlet, an outlet, and configured to contain fluid and couple to the housing; and a PTCR heating element configured to electrically couple to the power source and heat the fluid to form an aerosol. The PTCR heating element includes an electrical resistivity that varies based on temperature. The electrical resistivity includes an electrical resistivity transition zone including an increase in electrical resistivity over a temperature range such that, when the PTCR heating element reaches a temperature within the transition zone such that the element's resistivity increases to a level that limits current flow from the battery and therefore limits further temperature increases of the PTCR heating element.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF DRAWINGS

The patent or application file contains at least one drawing executed in color. Copies of this patent or patent application publication with color drawing(s) will be provided by the Office upon request and payment of the necessary fee.

The accompanying drawings, which are incorporated into and constitute a part of this specification, show certain aspects of the subject matter disclosed herein and, together with the description, help explain some of the principles associated with the disclosed implementations. In the drawings:

FIG. 1C presents a table of resistivity vs. temperature curve data for the nonlinear PTCR semiconducting material illustrated in FIG. 1B, consistent with implementations of the current subject matter;

FIG. 2A illustrates a diagram of an example heating element that can enable improved vaporizer heating, consistent with implementations of the current subject matter;

FIG. 2B illustrates a cross section of the example heating element illustrated in FIG. 2A, consistent with implementations of the current subject matter;

FIG. 3A-FIG. 3E illustrate modeled temperatures of the example heater, consistent with implementations of the current subject matter;

When practical, similar reference numbers denote similar structures, features, or elements.

DETAILED DESCRIPTION

Figure 1A:
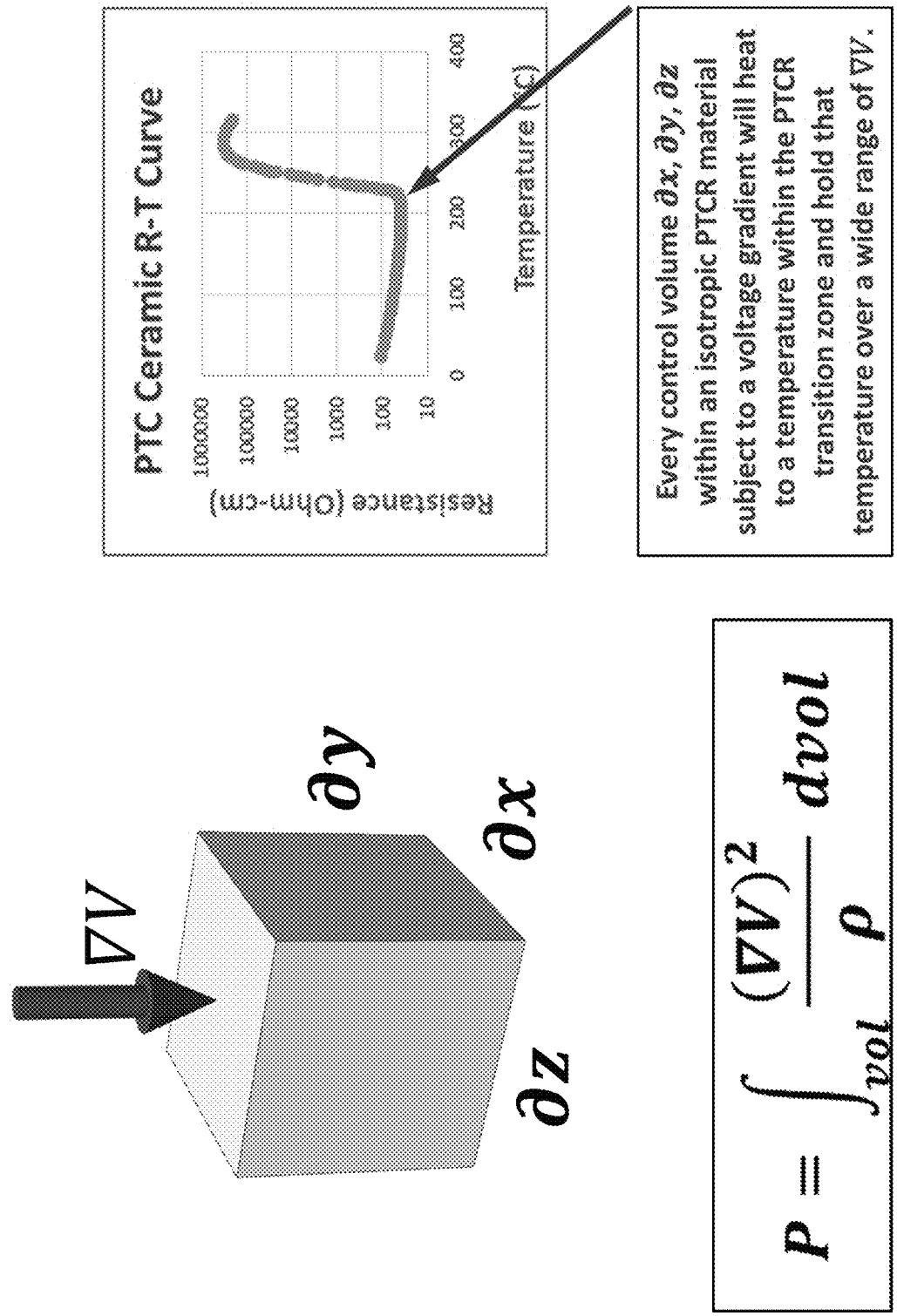
FIG. 1A illustrates the behavior of thermal power generation within an isotropic PTCR material.

Implementations of the current subject matter include methods, apparatuses, articles of manufacture, and systems relating to a vaporizer heater that utilizes a nonlinear positive temperature coefficient of resistivity (PTCR) heating element, also called a PTCR heater. It should be noted that "nonlinear" refers to the PTCR heating element over its operating range. While a portion of the operating range may exhibit a linear coefficient of resistivity, the coefficient of resistivity significantly changes at a transition temperature in which the rate of change of the coefficient of resistivity becomes greater by magnitudes. In this manner, a PTCR heating element can be temperature self-limiting, and given a known range of applied voltages, a sharp increase in resistance limits current flow so that the PTCR heating element will not heat beyond a specific operating temperature. By utilizing a PTCR heating element, some aspects of the current subject matter can enable a vaporizer device with intrinsic temperature control of the PTCR heating element at or near a desired operating temperature. Temperature can be controlled over a range of applied voltages and without the need for temperature sensors, electronic circuitry, controllers, microprocessors and/or algorithms providing power control to the PTCR heating element. By utilizing a PTCR heating element with intrinsic temperature control, overheating (e.g., burning) of the vaporizable material (e.g., a vaporizable fluid or other material) can be prevented, thereby avoiding formation of unwanted, and potentially dangerous, chemical byproducts.

One type of heating element can include a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the PTCR heating element.

Vaporizer devices can typically fall into two classes. One class of vaporizer device can be more sophisticated in that it utilizes relatively tight temperature control in order to prevent overheating and the formation of unwanted, and potentially dangerous, chemical byproducts. Such temperature control is typically expensive, in part because it may require hardware and/or software to measure temperature, such as one or more temperature sensors, and electronic circuitry, which may include a microprocessor, which may provide the ability to control power to a PTCR heating element at the point of vaporization.

Another class of vaporizer device can be simpler in that no temperature control may be provided, such that the construction of the vaporizer device may be less expensive but can include the danger of overheating the vaporizable material and/or various components of the vaporizer device and thereby causing permanent damage to the vaporizer device and/or the generation of unwanted chemical byproducts.

In some implementations, the current subject matter can enable a vaporizer device with a PTCR heating element and including simpler electronics, lower cost, and intrinsic and accurate temperature control.

A material's coefficient of resistivity characterizes a resistivity change in response to a temperature change of the PTCR heating element. Some implementations of the current subject matter include a PTCR heating element including a nonlinear positive temperature coefficient of resistivity (PTCR) which can include materials (e.g., semiconductors) that possess an electrical resistivity (also referred to as resistivity) that changes nonlinearly with increasing temperature. For example, the PTCR heating element can include a material with resistivity versus temperature characteristics that include a region (e.g., transition zone) in which there is a relatively large increase in resistivity over a relatively short period of temperature change, and thus can be referred to as being a nonlinear PTCR material. Such a PTCR heating element with a nonlinear PTCR material can be referred to as a PTCR heating element.

In such a PTCR heating element, the PTCR material resistivity can be relatively low while temperature remains below a temperature transition zone. Above the temperature transition zone, the PTCR material resistivity can be much higher than the resistivity of the same PTCR material at temperatures below the temperature transition zone. For example, the resistivity change can be orders of magnitude increase over a temperature transition zone of 50 degrees Celsius or less.

A PTCR heating element can utilize nonlinear PTCR material to enable intrinsic temperature control. For example, a PTCR heating element at an ambient temperature can be connected to a power source providing a voltage gradient and resulting current flow. Because the resistivity of the PTCR heating element is relatively low at ambient temperature (e.g., ambient temperature is below the transition zone), current will flow through the PTCR heating element. As current flows through the nonlinear PTCR material, heat is generated by resistance (e.g., dissipation of electrical power). The generated heat raises the temperature of the PTCR heating element, thereby causing the resistivity of the PTCR heating element to change. When the temperature of the PTCR heating element reaches the transition zone (i.e. at the transition temperature), the resistivity increases significantly over a small temperature range. The change in resistivity can be caused by a change in the physical properties of the material. For example, a phase transition may occur in the material. Such an increase in resistivity (resulting in an overall increase in resistance) reduces the current flow such that heat generation is reduced. The transition zone includes a temperature at which there is an inflection point such that heat generation will be insufficient to further raise the temperature of the PTCR heating element, thereby limiting the temperature of the PTCR heating element. So long as the power source remains connected and supplying current, the PTCR heating element will maintain a uniform temperature with minimal temperature variance. In this instance the applied power to the PTCR heating element can be represented by the equation $P_f = \text{Volts}^2/\text{Resistance}$. The heat loss of the PTCR heating element can be represented by $P_L$ and includes any combination of conductive, convective, radiative, and latent heat. During steady-state operation $P_f = P_L$. As $P_L$ increases, the temperature of the PTCR heating element drops thereby reducing the resistance thereby increasing the current flow through the PTCR heating element. As $P_L$ decreases, the temperature of the PTCR heating element increases thereby increasing the resistance thereby decreasing the current flow through the PTCR heating element. As $P_L$ approaches 0, the resistance of the PTCR heating element increase logarithmically. The operating temperature at which a PTCR heating element is limited can be affected by the element materials, element geometry, element resistivity as a function of temperature characteristics, power source, circuit characteristics (e.g., voltage gradient, current, time-variance properties), and the like.

The material structure of a PTCR heating element consistent with the current disclosure may be composed of many individual crystallites. At the edge of these individual crystallites are grain boundaries where potential barriers are formed, which prevent free electrons from diffusing into adjacent areas. This means that the grain boundaries would result in a high resistance, however, at low temperatures the effect is not present. Without being bounded to any particular theory, it is believed that high dielectric constants and sudden polarization at the grain boundaries prevent the formation of potential barriers at lower temperatures to enable a flow of free electrons (i.e. current flow). Above a higher temperature, known as a Curie temperature, the dielectric constant and polarization drop to the point that there is a strong growth of the potential barriers and thus a rise in electrical resistance. In a certain range of temperatures above a Curie temperature, the resistance of the PTCR heating element increases exponentially.

The thermal power generation within an isotropic PTCR material can be characterized such that, for every control volume $\partial x$, $\partial y$, $\partial z$ within an isotropic PTCR material subject to a voltage gradient $\nabla V$, the control volume $\partial x$, $\partial y$, $\partial z$ will heat to a temperature within the PTCR transition zone and hold that temperature within a wide range of $\nabla V$ as illustrated in FIG. 1A. Thermal power generation can be expressed as:

$$P = \int_{vol} \frac{(\nabla V)^2}{\rho} dvol,$$

where P is thermal power generation, vol is the control volume (e.g., $\partial x$, $\partial y$, $\partial z$), and $\rho$ is resistivity.

Figure 1B:
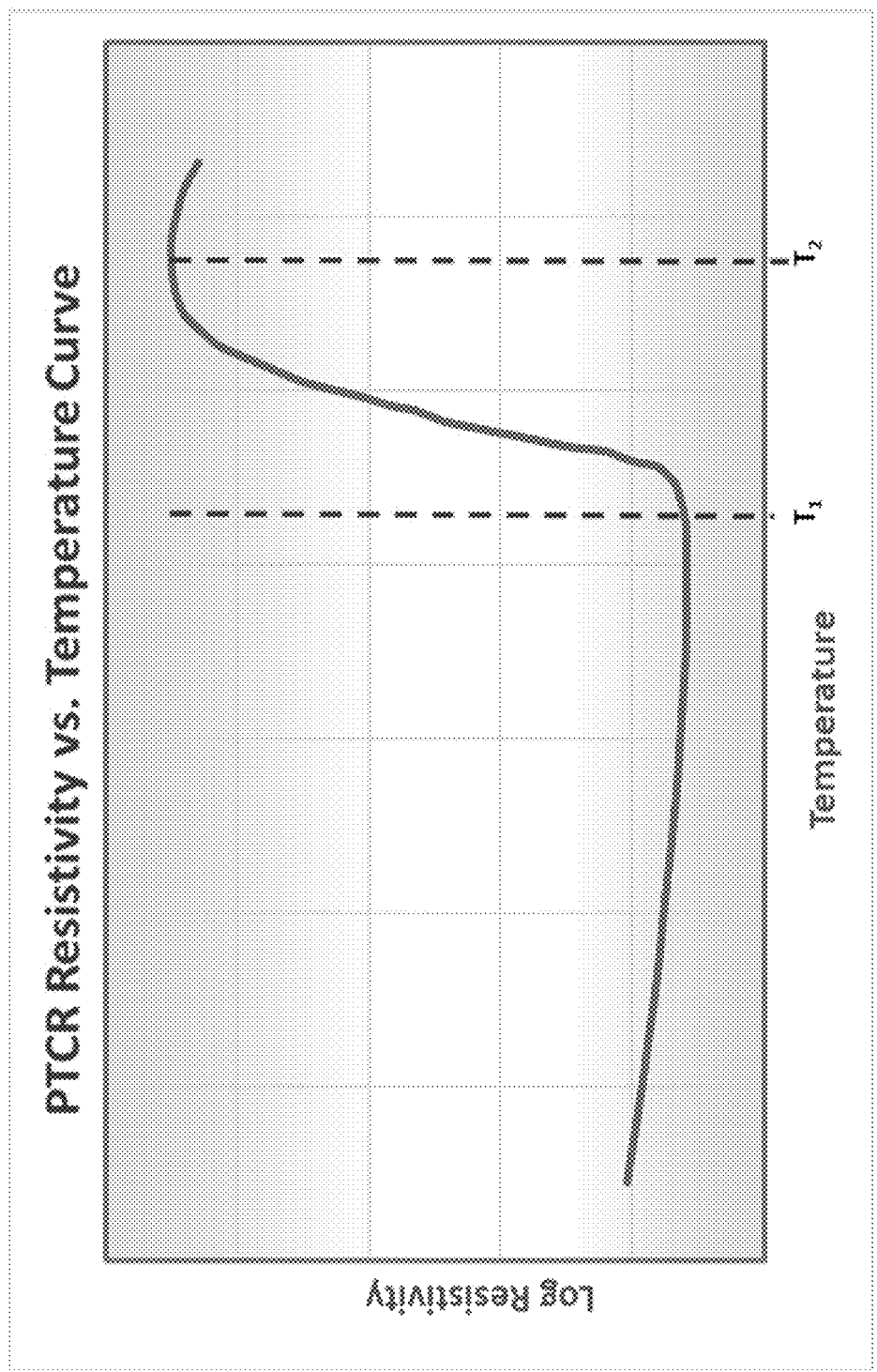
FIG. 1B illustrates a plot illustrating an example resistivity vs. temperature curve for a nonlinear positive temperature coefficient of resistivity semiconducting material, consistent with implementations of the current subject matter.

FIG. 1B is a plot illustrating an example resistivity vs. temperature curve for a nonlinear PTCR material. The vertical axis is logarithmic. A PTCR heating element constructed (e.g., formed) of a nonlinear PTCR material (referred to as a PTCR heater) can include advantageous characteristics. For example, with application of sufficient voltage gradient (e.g., $\nabla V$), a PTCR heater will generate heat and increase in temperature until the transition zone is reached. In the curve illustrated in FIG. 1B, the transition zone spans between temperatures $T_1$ and $T_2$. In the curve illustrated in FIG. 1B, the resistivity versus temperature curve appears nonlinear between $T_1$ and $T_2$, but in other embodiments, the resistivity versus temperature curve may be near linear or linear or other shapes. At some temperature above Ti, the resistivity of the nonlinear PTCR material will have increased to the point where further temperature increase will cease because the overall resistance will increase to a point such that current flow is limited. In other words, implementations of a PTCR heater can be considered to be temperature self-limiting and, given a known range of applied voltages, will not heat beyond a temperature just above the low point Ti of the temperature transition zone. In the curve illustrated in FIG. 1B, the resistivity decreases as the temperature increases to Ti, but in other embodiments, the resistivity may be more level or even increase as the temperature increases to Ti.

FIG. 1C presents a table of resistivity vs. temperature curve data for the nonlinear PTCR semiconducting material illustrated in FIG. 1B. In some implementations, the PTCR heating element has a resistivity of between 10 ohm-cm and 100 ohm-cm at 100° C. and a resistivity of between 50000 ohm-cm and 150000 ohm-cm at 260° C. In some implementations, the PTCR heating element has a resistivity of between 20 ohm-cm and 200 ohm-cm at 100° C. and a resistivity of between 100000 ohm-cm and 200000 ohm-cm at 265° C. In some implementations, the PTCR heating element has a resistivity of less than 100 ohm-cm at 100° C. and a resistivity greater than 100000 ohm-cm at 260° C. In some implementations, the PTCR heating element has a resistivity of less than 100 ohm-cm at 100° C. and a resistivity greater than 250000 ohm-cm at 275° C. In some implementations, the PTCR heating element has a resistivity of less than 100 ohm-cm at 100° C. and a resistivity greater than 300000 ohm-cm at 295° C. In some implementations, the PTCR heating element has a resistivity of between 10 ohm-cm and 110 ohm-cm at 25° C. and a resistivity of between 10 ohm-cm and 110 ohm-cm at 100° C. and a resistivity of between 100000 ohm-cm and 325000 ohm-cm at 280° C. In some implementations, the PTCR heating element has a resistivity of between 10 ohm-cm and 150 ohm-cm at 25° C. and a resistivity of between 10 ohm-cm and 150 ohm-cm at 100° C. and a resistivity of between 100000 ohm-cm and 350000 ohm-cm at 280° C. In some implementations, the PTCR heating element has a resistivity of between 10 ohm-cm and 200 ohm-cm at 25° C. and a resistivity of between 10 ohm-cm and 200 ohm-cm at 100° C. and a resistivity of between 100000 ohm-cm and 375000 ohm-cm at 280° C. In some implementations, the PTCR heating element has a resistivity of between 10 ohm-cm and 300 ohm-cm at 25° C. and a resistivity of between 10 ohm-cm and 300 ohm-cm at 100° C. and a resistivity of between 100000 ohm-cm and 400000 ohm-cm at 280° C. In some implementations, the PTCR heating element has a resistivity of between 10 ohm-cm and 400 ohm-cm at 25° C. and a resistivity of between 10 ohm-cm and 400 ohm-cm at 100° C. and a resistivity of between 100000 ohm-cm and 450000 ohm-cm at 280° C. In some implementations, the PTCR heating element has a resistivity of between 10 ohm-cm and 500 ohm-cm at 25° C. and a resistivity of between 10 ohm-cm and 500 ohm-cm at 100° C. and a resistivity of between 100000 ohm-cm and 500000 ohm-cm at 280° C. In some implementations, the PTCR heating element has a resistivity of between 50 ohm-cm and 110 ohm-cm at 25° C. and a resistivity of between 50 ohm-cm and 110 ohm-cm at 100° C. and a resistivity of between 150000 ohm-cm and 325000 ohm-cm at 280° C. In some implementations, the PTCR heating element has a resistivity of between 50 ohm-cm and 150 ohm-cm at 25° C. and a resistivity of between 50 ohm-cm and 150 ohm-cm at 100° C. and a resistivity of between 150000 ohm-cm and 350000 ohm-cm at 280° C. In some implementations, the PTCR heating element has a resistivity of between 50 ohm-cm and 200 ohm-cm at 25° C. and a resistivity of between 50 ohm-cm and 200 ohm-cm at 100° C. and a resistivity of between 150000 ohm-cm and 375000 ohm-cm at 280° C. In some implementations, the PTCR heating element has a resistivity of between 50 ohm-cm and 300 ohm-cm at 25° C. and a resistivity of between 50 ohm-cm and 300 ohm-cm at 100° C. and a resistivity of between 150000 ohm-cm and 400000 ohm-cm at 280° C. In some implementations, the PTCR heating element has a resistivity of between 50 ohm-cm and 400 ohm-cm at 25° C. and a resistivity of between 50 ohm-cm and 400 ohm-cm at 100° C. and a resistivity of between 150000 ohm-cm and 450000 ohm-cm at 280° C. In some implementations, the PTCR heating element has a resistivity of between 50 ohm-cm and 500 ohm-cm at 25° C. and a resistivity of between 50 ohm-cm and 500 ohm-cm at 100° C. and a resistivity of between 150000 ohm-cm and 500000 ohm-cm at 280° C. In some implementations, the PTCR heating element has a resistivity of between 90 ohm-cm and 110 ohm-cm at 25° C. and a resistivity of between 90 ohm-cm and 110 ohm-cm at 100° C. and a resistivity of between 200000 ohm-cm and 325000 ohm-cm at 280° C. In some implementations, the PTCR heating element has a resistivity of between 90 ohm-cm and 150 ohm-cm at 25° C. and a resistivity of between 90 ohm-cm and 150 ohm-cm at 100° C. and a resistivity of between 200000 ohm-cm and 350000 ohm-cm at 280° C. In some implementations, the PTCR heating element has a resistivity of between 90 ohm-cm and 200 ohm-cm at 25° C. and a resistivity of between 90 ohm-cm and 200 ohm-cm at 100° C. and a resistivity of between 200000 ohm-cm and 375000 ohm-cm at 280° C. In some implementations, the PTCR heating element has a resistivity of between 90 ohm-cm and 300 ohm-cm at 25° C. and a resistivity of between 90 ohm-cm and 300 ohm-cm at 100° C. and a resistivity of between 200000 ohm-cm and 400000 ohm-cm at 280° C. In some implementations, the PTCR heating element has a resistivity of between 90 ohm-cm and 400 ohm-cm at 25° C. and a resistivity of between 90 ohm-cm and 400 ohm-cm at 100° C. and a resistivity of between 200000 ohm-cm and 450000 ohm-cm at 280° C. In some implementations, the PTCR heating element has a resistivity of between 90 ohm-cm and 500 ohm-cm at 25° C. and a resistivity of between 90 ohm-cm and 500 ohm-cm at 100° C. and a resistivity of between 200000 ohm-cm and 500000 ohm-cm at 280° C. In some implementations, the PTCR heating element has a resistivity of between 10 ohm-cm and 110 ohm-cm at 50° C. and a resistivity of between 10 ohm-cm and 50 ohm-cm at 150° C. and a resistivity of between 50000 ohm-cm and 125000 ohm-cm at 260° C. In some implementations, the PTCR heating element has a resistivity of between 10 ohm-cm and 150 ohm-cm at 50° C. and a resistivity of between 10 ohm-cm and 100 ohm-cm at 150° C. and a resistivity of between 50000 ohm-cm and 150000 ohm-cm at 260° C. In some implementations, the PTCR heating element has a resistivity of between 10 ohm-cm and 200 ohm-cm at 50° C. and a resistivity of between 10 ohm-cm and 150 ohm-cm at 150° C. and a resistivity of between 50000 ohm-cm and 175000 ohm-cm at 260° C. In some implementations, the PTCR heating element has a resistivity of between 10 ohm-cm and 300 ohm-cm at 50° C. and a resistivity of between 10 ohm-cm and 200 ohm-cm at 150° C. and a resistivity of between 50000 ohm-cm and 200000 ohm-cm at 260° C. In some implementations, the PTCR heating element has a resistivity of between 10 ohm-cm and 400 ohm-cm at 50° C. and a resistivity of between 10 ohm-cm and 250 ohm-cm at 150° C. and a resistivity of between 50000 ohm-cm and 250000 ohm-cm at 260° C. In some implementations, the PTCR heating element has a resistivity of between 10 ohm-cm and 500 ohm-cm at 50° C. and a resistivity of between 10 ohm-cm and 300 ohm-cm at 150° C. and a resistivity of between 50000 ohm-cm and 300000 ohm-cm at 260° C. In some implementations, the PTCR heating element has a resistivity of between 50 ohm-cm and 110 ohm-cm at 50° C. and a resistivity of between 20 ohm-cm and 50 ohm-cm at 150° C. and a resistivity of between 75000 ohm-cm and 125000 ohm-cm at 260° C. In some implementations, the PTCR heating element has a resistivity of between 50 ohm-cm and 150 ohm-cm at 50° C. and a resistivity of between 20 ohm-cm and 100 ohm-cm at 150° C. and a resistivity of between 75000 ohm-cm and 150000 ohm-cm at 260° C. In some implementations, the PTCR heating element has a resistivity of between 50 ohm-cm and 200 ohm-cm at 50° C. and a resistivity of between 20 ohm-cm and 150 ohm-cm at 150° C. and a resistivity of between 75000 ohm-cm and 175000 ohm-cm at 260° C. In some implementations, the PTCR heating element has a resistivity of between 50 ohm-cm and 300 ohm-cm at 50° C. and a resistivity of between 20 ohm-cm and 200 ohm-cm at 150° C. and a resistivity of between 75000 ohm-cm and 200000 ohm-cm at 260° C. In some implementations, the PTCR heating element has a resistivity of between 50 ohm-cm and 400 ohm-cm at 50° C. and a resistivity of between 20 ohm-cm and 250 ohm-cm at 150° C. and a resistivity of between 75000 ohm-cm and 250000 ohm-cm at 260° C. In some implementations, the PTCR heating element has a resistivity of between 50 ohm-cm and 500 ohm-cm at 50° C. and a resistivity of between 20 ohm-cm and 300 ohm-cm at 150° C. and a resistivity of between 75000 ohm-cm and 300000 ohm-cm at 260° C. In some implementations, the PTCR heating element has a resistivity of between 75 ohm-cm and 110 ohm-cm at 50° C. and a resistivity of between 30 ohm-cm and 50 ohm-cm at 150° C. and a resistivity of between 100000 ohm-cm and 125000 ohm-cm at 260° C. In some implementations, the PTCR heating element has a resistivity of between 75 ohm-cm and 150 ohm-cm at 50° C. and a resistivity of between 30 ohm-cm and 100 ohm-cm at 150° C. and a resistivity of between 100000 ohm-cm and 150000 ohm-cm at 260° C. In some implementations, the PTCR heating element has a resistivity of between 75 ohm-cm and 200 ohm-cm at 50° C. and a resistivity of between 30 ohm-cm and 150 ohm-cm at 150° C. and a resistivity of between 100000 ohm-cm and 175000 ohm-cm at 260° C. In some implementations, the PTCR heating element has a resistivity of between 75 ohm-cm and 300 ohm-cm at 50° C. and a resistivity of between 30 ohm-cm and 200 ohm-cm at 150° C. and a resistivity of between 100000 ohm-cm and 200000 ohm-cm at 260° C. In some implementations, the PTCR heating element has a resistivity of between 75 ohm-cm and 400 ohm-cm at 50° C. and a resistivity of between 30 ohm-cm and 250 ohm-cm at 150° C. and a resistivity of between 100000 ohm-cm and 250000 ohm-cm at 260° C. In some implementations, the PTCR heating element has a resistivity of between 75 ohm-cm and 500 ohm-cm at 50° C. and a resistivity of between 30 ohm-cm and 300 ohm-cm at 150° C. and a resistivity of between 100000 ohm-cm and 300000 ohm-cm at 260° C. In some implementations, the PTCR heating element has a resistivity of between 10 ohm-cm and 110 ohm-cm at 25° C. and a resistivity of between 10 ohm-cm and 50 ohm-cm at 150° C. and a resistivity of between 100000 ohm-cm and 325000 ohm-cm at 280° C. In some implementations, the PTCR heating element has a resistivity of between 10 ohm-cm and 150 ohm-cm at 25° C. and a resistivity of between 10 ohm-cm and 100 ohm-cm at 150° C. and a resistivity of between 100000 ohm-cm and 350000 ohm-cm at 280° C. In some implementations, the PTCR heating element has a resistivity of between 10 ohm-cm and 200 ohm-cm at 25° C. and a resistivity of between 10 ohm-cm and 150 ohm-cm at 150° C. and a resistivity of between 100000 ohm-cm and 375000 ohm-cm at 280° C. In some implementations, the PTCR heating element has a resistivity of between 10 ohm-cm and 300 ohm-cm at 25° C. and a resistivity of between 10 ohm-cm and 200 ohm-cm at 150° C. and a resistivity of between 100000 ohm-cm and 400000 ohm-cm at 280° C. In some implementations, the PTCR heating element has a resistivity of between 10 ohm-cm and 400 ohm-cm at 25° C. and a resistivity of between 10 ohm-cm and 250 ohm-cm at 150° C. and a resistivity of between 100000 ohm-cm and 450000 ohm-cm at 280° C. In some implementations, the PTCR heating element has a resistivity of between 10 ohm-cm and 500 ohm-cm at 25° C. and a resistivity of between 10 ohm-cm and 300 ohm-cm at 150° C. and a resistivity of between 100000 ohm-cm and 500000 ohm-cm at 280° C. In some implementations, the PTCR heating element has a resistivity of between 50 ohm-cm and 110 ohm-cm at 25° C. and a resistivity of between 20 ohm-cm and 50 ohm-cm at 150° C. and a resistivity of between 150000 ohm-cm and 325000 ohm-cm at 280° C. In some implementations, the PTCR heating element has a resistivity of between 50 ohm-cm and 150 ohm-cm at 25° C. and a resistivity of between 20 ohm-cm and 100 ohm-cm at 150° C. and a resistivity of between 150000 ohm-cm and 350000 ohm-cm at 280° C. In some implementations, the PTCR heating element has a resistivity of between 50 ohm-cm and 200 ohm-cm at 25° C. and a resistivity of between 20 ohm-cm and 150 ohm-cm at 150° C. and a resistivity of between 150000 ohm-cm and 375000 ohm-cm at 280° C. In some implementations, the PTCR heating element has a resistivity of between 50 ohm-cm and 300 ohm-cm at 25° C. and a resistivity of between 20 ohm-cm and 200 ohm-cm at 150° C. and a resistivity of between 150000 ohm-cm and 400000 ohm-cm at 280° C. In some implementations, the PTCR heating element has a resistivity of between 50 ohm-cm and 400 ohm-cm at 25° C. and a resistivity of between 20 ohm-cm and 250 ohm-cm at 150° C. and a resistivity of between 150000 ohm-cm and 450000 ohm-cm at 280° C. In some implementations, the PTCR heating element has a resistivity of between 50 ohm-cm and 500 ohm-cm at 25° C. and a resistivity of between 20 ohm-cm and 300 ohm-cm at 150° C. and a resistivity of between 150000 ohm-cm and 500000 ohm-cm at 280° C. In some implementations, the PTCR heating element has a resistivity of between 90 ohm-cm and 110 ohm-cm at 25° C. and a resistivity of between 30 ohm-cm and 50 ohm-cm at 150° C. and a resistivity of between 200000 ohm-cm and 325000 ohm-cm at 280° C. In some implementations, the PTCR heating element has a resistivity of between 90 ohm-cm and 150 ohm-cm at 25° C. and a resistivity of between 30 ohm-cm and 100 ohm-cm at 150° C. and a resistivity of between 200000 ohm-cm and 350000 ohm-cm at 280° C. In some implementations, the PTCR heating element has a resistivity of between 90 ohm-cm and 200 ohm-cm at 25° C. and a resistivity of between 30 ohm-cm and 150 ohm-cm at 150° C. and a resistivity of between 200000 ohm-cm and 375000 ohm-cm at 280° C. In some implementations, the PTCR heating element has a resistivity of between 90 ohm-cm and 300 ohm-cm at 25° C. and a resistivity of between 30 ohm-cm and 200 ohm-cm at 150° C. and a resistivity of between 200000 ohm-cm and 400000 ohm-cm at 280° C. In some implementations, the PTCR heating element has a resistivity of between 90 ohm-cm and 400 ohm-cm at 25° C. and a resistivity of between 30 ohm-cm and 250 ohm-cm at 150° C. and a resistivity of between 200000 ohm-cm and 450000 ohm-cm at 280° C. In some implementations, the PTCR heating element has a resistivity of between 90 ohm-cm and 500 ohm-cm at 25° C. and a resistivity of between 30 ohm-cm and 300 ohm-cm at 150° C. and a resistivity of between 200000 ohm-cm and 500000 ohm-cm at 280° C. In some implementations, the PTCR heating element has a resistivity of between 10 ohm-cm and 110 ohm-cm at 50° C. and a resistivity of between 10 ohm-cm and 110 ohm-cm at 100° C. and a resistivity of between 50000 ohm-cm and 125000 ohm-cm at 260° C. In some implementations, the PTCR heating element has a resistivity of between 10 ohm-cm and 150 ohm-cm at 50° C. and a resistivity of between 10 ohm-cm and 150 ohm-cm at 100° C. and a resistivity of between 50000 ohm-cm and 150000 ohm-cm at 260° C. In some implementations, the PTCR heating element has a resistivity of between 10 ohm-cm and 200 ohm-cm at 50° C. and a resistivity of between 10 ohm-cm and 200 ohm-cm at 100° C. and a resistivity of between 50000 ohm-cm and 175000 ohm-cm at 260° C. In some implementations, the PTCR heating element has a resistivity of between 10 ohm-cm and 300 ohm-cm at 50° C. and a resistivity of between 10 ohm-cm and 300 ohm-cm at 100° C. and a resistivity of between 50000 ohm-cm and 200000 ohm-cm at 260° C. In some implementations, the PTCR heating element has a resistivity of between 10 ohm-cm and 400 ohm-cm at 50° C. and a resistivity of between 10 ohm-cm and 400 ohm-cm at 100° C. and a resistivity of between 50000 ohm-cm and 250000 ohm-cm at 260° C. In some implementations, the PTCR heating element has a resistivity of between 10 ohm-cm and 500 ohm-cm at 50° C. and a resistivity of between 10 ohm-cm and 500 ohm-cm at 100° C. and a resistivity of between 50000 ohm-cm and 300000 ohm-cm at 260° C. In some implementations, the PTCR heating element has a resistivity of between 50 ohm-cm and 110 ohm-cm at 50° C. and a resistivity of between 50 ohm-cm and 110 ohm-cm at 100° C. and a resistivity of between 75000 ohm-cm and 125000 ohm-cm at 260° C. In some implementations, the PTCR heating element has a resistivity of between 50 ohm-cm and 150 ohm-cm at 50° C. and a resistivity of between 50 ohm-cm and 150 ohm-cm at 100° C. and a resistivity of between 75000 ohm-cm and 150000 ohm-cm at 260° C. In some implementations, the PTCR heating element has a resistivity of between 50 ohm-cm and 200 ohm-cm at 50° C. and a resistivity of between 50 ohm-cm and 200 ohm-cm at 100° C. and a resistivity of between 75000 ohm-cm and 175000 ohm-cm at 260° C. In some implementations, the PTCR heating element has a resistivity of between 50 ohm-cm and 300 ohm-cm at 50° C. and a resistivity of between 50 ohm-cm and 300 ohm-cm at 100° C. and a resistivity of between 75000 ohm-cm and 200000 ohm-cm at 260° C. In some implementations, the PTCR heating element has a resistivity of between 50 ohm-cm and 400 ohm-cm at 50° C. and a resistivity of between 50 ohm-cm and 400 ohm-cm at 100° C. and a resistivity of between 75000 ohm-cm and 250000 ohm-cm at 260° C. In some implementations, the PTCR heating element has a resistivity of between 50 ohm-cm and 500 ohm-cm at 50° C. and a resistivity of between 50 ohm-cm and 500 ohm-cm at 100° C. and a resistivity of between 75000 ohm-cm and 300000 ohm-cm at 260° C. In some implementations, the PTCR heating element has a resistivity of between 75 ohm-cm and 110 ohm-cm at 50° C. and a resistivity of between 90 ohm-cm and 110 ohm-cm at 100° C. and a resistivity of between 100000 ohm-cm and 125000 ohm-cm at 260° C. In some implementations, the PTCR heating element has a resistivity of between 75 ohm-cm and 150 ohm-cm at 50° C. and a resistivity of between 90 ohm-cm and 150 ohm-cm at 100° C. and a resistivity of between 100000 ohm-cm and 150000 ohm-cm at 260° C. In some implementations, the PTCR heating element has a resistivity of between 75 ohm-cm and 200 ohm-cm at 50° C. and a resistivity of between 90 ohm-cm and 200 ohm-cm at 100° C. and a resistivity of between 100000 ohm-cm and 175000 ohm-cm at 260° C. In some implementations, the PTCR heating element has a resistivity of between 75 ohm-cm and 300 ohm-cm at 50° C. and a resistivity of between 90 ohm-cm and 300 ohm-cm at 100° C. and a resistivity of between 100000 ohm-cm and 200000 ohm-cm at 260° C. In some implementations, the PTCR heating element has a resistivity of between 75 ohm-cm and 400 ohm-cm at 50° C. and a resistivity of between 90 ohm-cm and 400 ohm-cm at 100° C. and a resistivity of between 100000 ohm-cm and 250000 ohm-cm at 260° C. In some implementations, the PTCR heating element has a resistivity of between 75 ohm-cm and 500 ohm-cm at 50° C. and a resistivity of between 90 ohm-cm and 500 ohm-cm at 100° C. and a resistivity of between 100000 ohm-cm and 300000 ohm-cm at 260° C.

Performance of a PTCR heater can depend on PTCR behavior as in FIG. 1B and on heater geometry. A PTCR heater having relatively long and narrow geometry and with electrical contacts for applying differential voltage at each end of the longer dimension of the PTCR heater can be ineffective in that resistivity of nonlinear PTCR materials is typically too high at temperatures below $T_1$. Nonlinear PTCR materials having steep transition zones where the temperature difference between $T_1$ and $T_2$ is less than 10° C. may cause all voltage drop to be within a small fraction of the length of said long and narrow geometry and given inevitable spatial non-uniformities within any material. Therefore, some implementations of a PTCR heater include an electrode construct for a PTCR heater such that a nonlinear PTCR material is provided within a parallel circuit. In some implementations that can provide improved uniformity in heating. The PTCR heater geometry can include a thin section of nonlinear PTCR material sandwiched between electrical conductors or electrically conductive coatings to which differential voltages may be applied.

FIG. 2A is a diagram illustrating an example PTCR heating element 50 that can enable improved vaporizer heating. A thin section of nonlinear PTCR material 10 (e.g. a PTCR ceramic material) is shown in FIG. 2, where nonlinear PTCR material 10 is sandwiched between electrically conductive layers 20, which in turn are attached to conductive leads 30 such that conductive leads 30 may have differential voltage applied. In some implementations, a single conductive lead 20 is attached to each electrically conductive layer 20 of the PTCR heating element 50. In some implementations, two or more conductive leads 20 are attached to each electrically conductive layer 20 of the PTCR heating element 50. FIG. 2B is a cross section of the example PTCR heating element 50 illustrated in FIG. 2A.

In some implementations, which can be effective in a vaporizer device using a vaporizable material, for example, a fluid can be a combination including propylene glycol and glycerol. In some implementations, the fluid is a vaporizable material comprising a nicotine formulation. In some implementations, a PTCR heating element 50 includes the geometry illustrated in FIG. 2A with nonlinear PTCR material thickness of 0.5 mm (height) and 5.0 mm (length and width) in the other dimensions. PTCR material thickness, in some exemplary embodiments, can be about 0.2 mm to about 0.5 mm. The nonlinear PTCR material electrical characteristics includes these values: $T_1$ value between 150° C. and 300° C., such as between 220° C. and 280° C.; Resistivity at temperatures below $T_1$ between 0.1 Ohm-m and 100 Ohm-m, such as between 1 Ohm-m and 10 Ohm-m; Resistivity change between $T_1$ and $T_2$ having an increase of a factor exceeding 100 such as exceeding 1000; and temperature difference between $T_1$ and $T_2$ less than 200° C. such as less than 50° C.

Figure 3E:
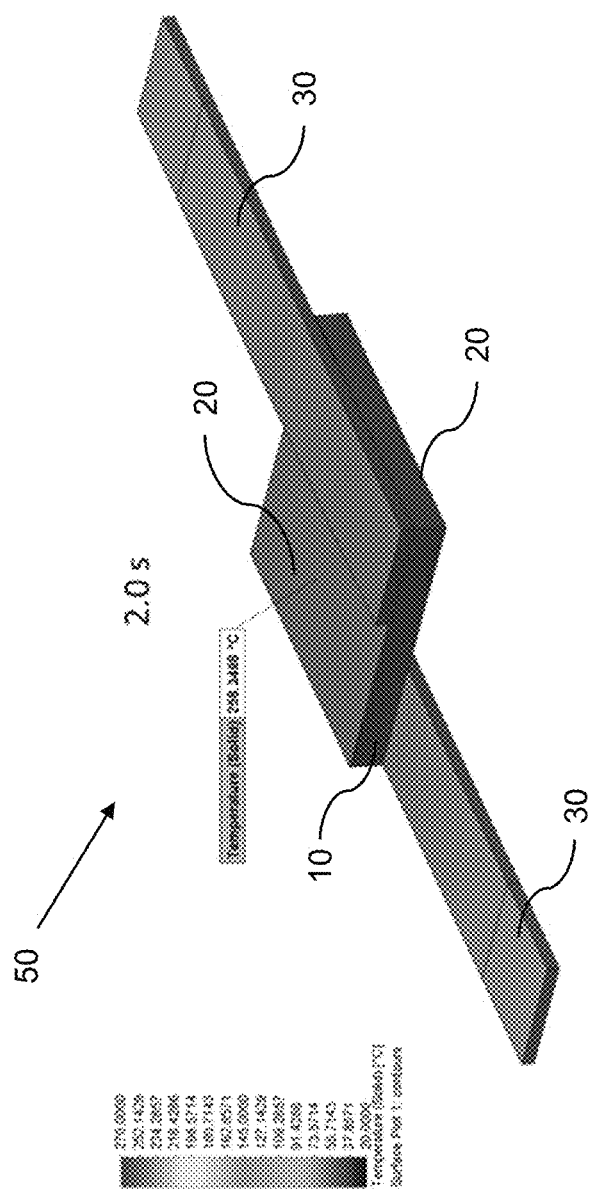
Figure 3F:
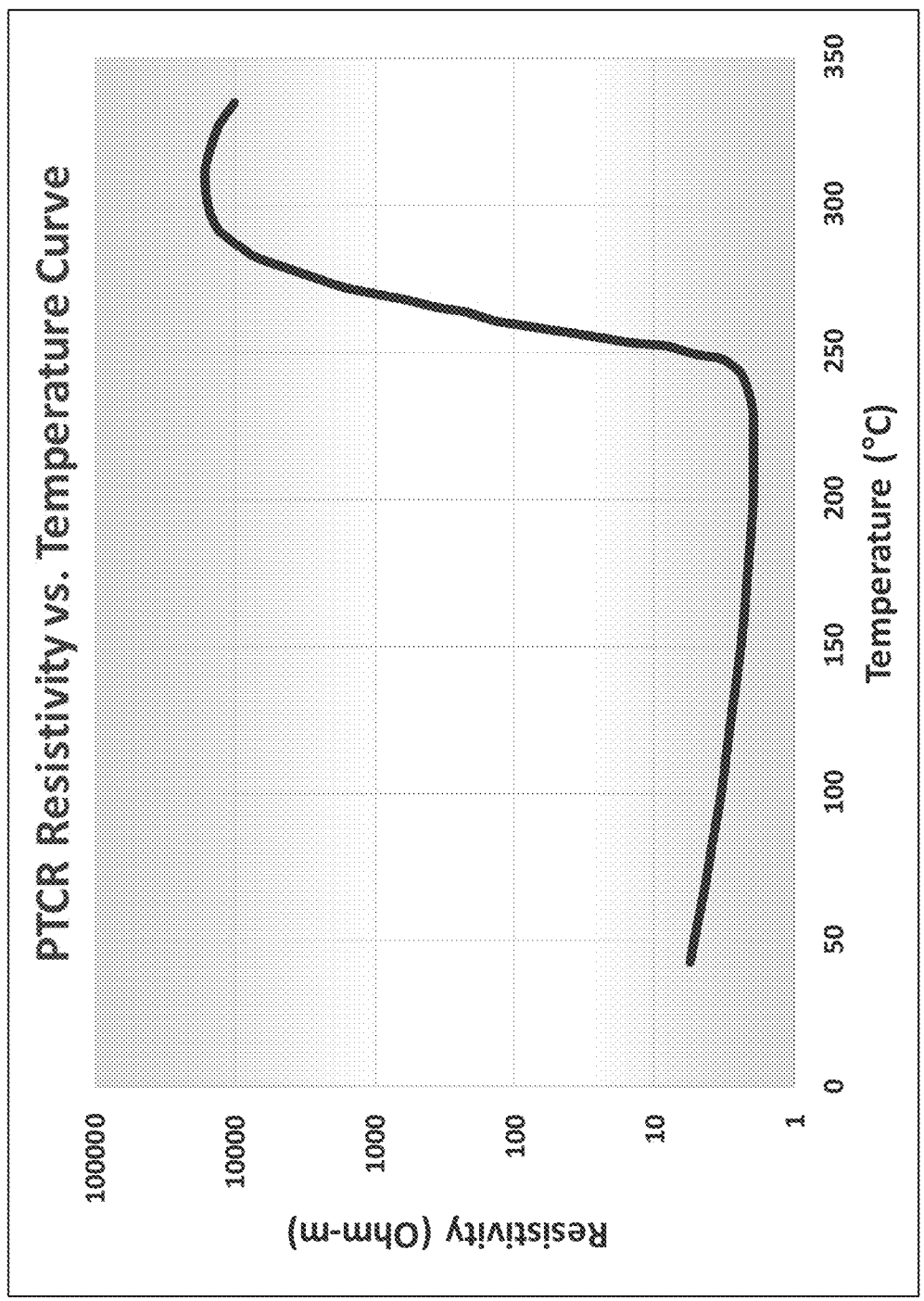
FIG. 3F illustrates an example nonlinear PTCR resistivity versus temperature curve, consistent with implementations of the current subject matter.

FIG. 3A-FIG. 3E illustrate modeled temperatures of an example of a PTCR heating element 50. In the illustrated examples, the nonlinear PTCR material 10 includes a plate geometry with dimensions of 5 mm×5 mm×0.5 mm; the conductive layers 20 were formed of silver (Ag) with dimensions of 5 mm×5 mm×0.025 mm; and the conductive leads 30 were formed of copper (CU) with dimensions of 12 mm×2 mm×0.2 mm. The plate geometry can include two parallel sides with conductive leads attached thereto. The nonlinear PTCR material 10 included a PTCR resistivity versus temperature curve as illustrated in FIG. 3F, with a nonlinear transition zone of about 240° C. to about 300° C. A voltage of 3 volts to 6 volts was applied across the conductive leads 30 of the example PTCR heating element 50. With other configurations, different voltage ranges may be applied such as, for example, 3 volts to 10 volts, 3 volts to 50 volts, etc. Under these circumstances, the example PTCR heating element 50 in open air with free convective airflow will increase in temperature as shown in the modeled sequence of FIG. 3A-FIG. 3E, which illustrate respectively 0.0, 0.2, 0.5, 1.0, and 2.0 seconds after application of the voltage differential. As illustrated, the temperature beyond 1.0 second is relatively uniform and the peak temperatures at the surface of conductive layers 20 is less than 270° C.

Figure 3G:
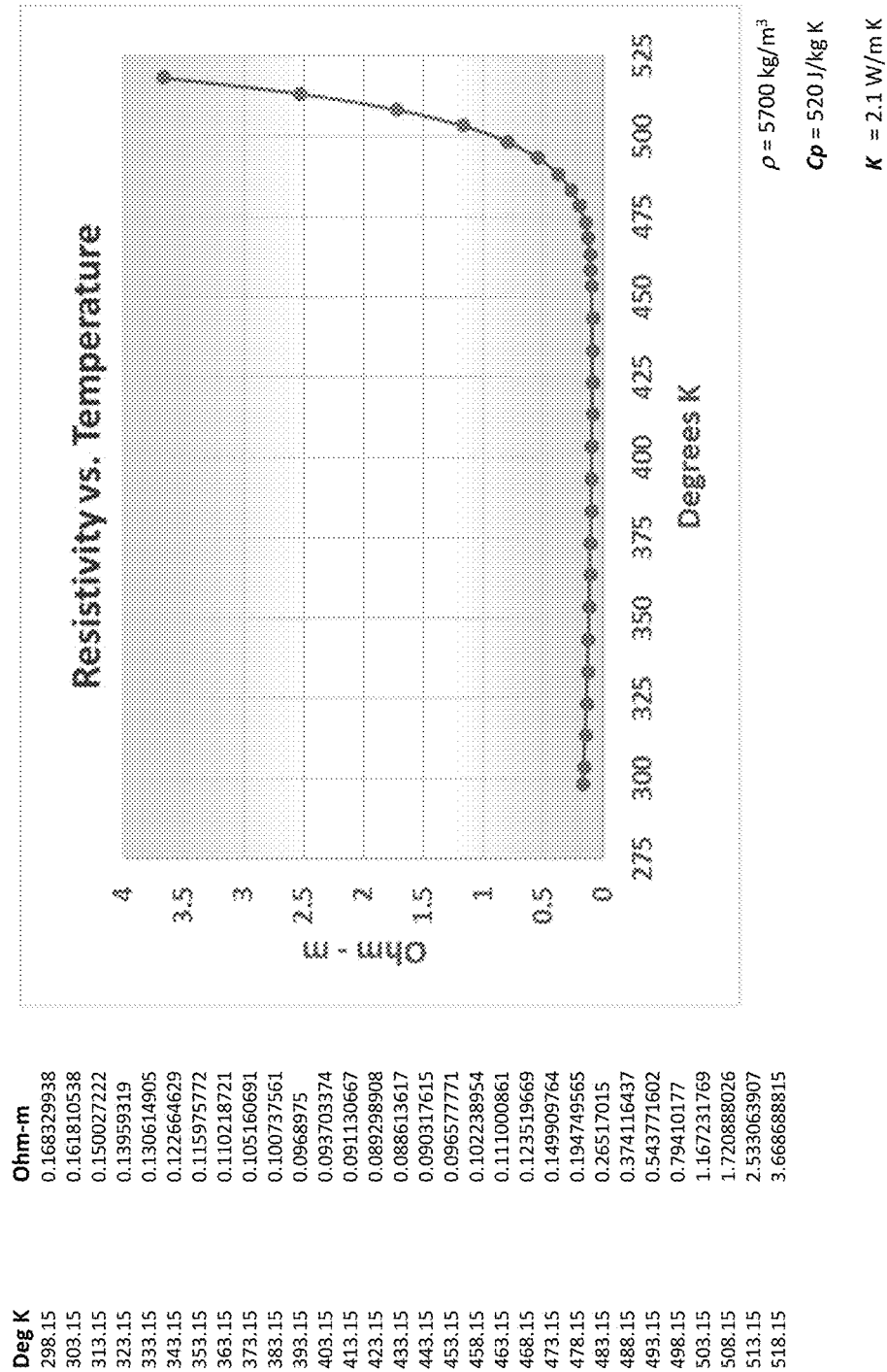
FIG. 3G illustrates another example PTCR resistivity versus temperature curve, consistent with implementations of the current subject matter.

FIG. 3G illustrates another example PTCR resistivity versus temperature curve. In this example, the PTCR material has a density of 5700 kg/m3, a heat capacity of 520 J/kg K, and a thermal conductivity of 2.1 W/m K. The coefficient of resistivity begins to initially increase at a temperature after about 440 K and then sharply increases between 503 K and 518 K. At 298 K, the resistivity of the PTCR material forming the PTCR heating element is 0.168 ohm-m, and at 373 K the resistivity of the PTCR material forming the PTCR heating element is 0.105 ohm-m, and at 518 K the resistivity of the PTCR material forming the PTCR heating element is 3.669 ohm-m. In some example implementations, the PTCR material has a density between 5000 kg/m3 and 7000 kg/m3, a heat capacity between 450 J/kg K and 600 J/kg K, and a thermal conductivity between 1.5 W/m K and 3.0 W/m K.

Uniform temperature can be a desirable performance attribute of PTCR heaters, providing a distinct advantage over series coil heaters, including series heaters having power input controlled by temperature sensors, electronic circuits with microprocessors, and sophisticated algorithms dedicated to the purpose of temperature control. The existing series heaters can have overall power modulated in response to temperature measurement at a point or by average temperature estimated by overall electrical resistivity in combination with TCR (temperature coefficient of resistivity) of the typical series heating element. However, in some series heaters, temperatures within the series heater can vary by 40° C. or more because overall power is modulated and local temperatures can vary due to, for example, variations in local resistivity.

In some implementations, a PTCR heating element 50 may be constructed with material having a nonlinear PTCR resistivity vs. temperature curve the same or similar to that shown in FIG. 1B, with parallel geometry such as that shown in FIG. 2A and FIG. 2B, and with an adequate (e.g., 3 V to 6 V) differential voltage applied to conductive leads 30, each of a given control volume within such a PTCR heater will have a temperature within a narrow range, typically less than 10° C. This can be achieved even with differential thermal loading. The less than 10° C. range can be tailored for vaporization by controlling the materials and geometric arrangement of the PTCR heating element.

Figure 4:
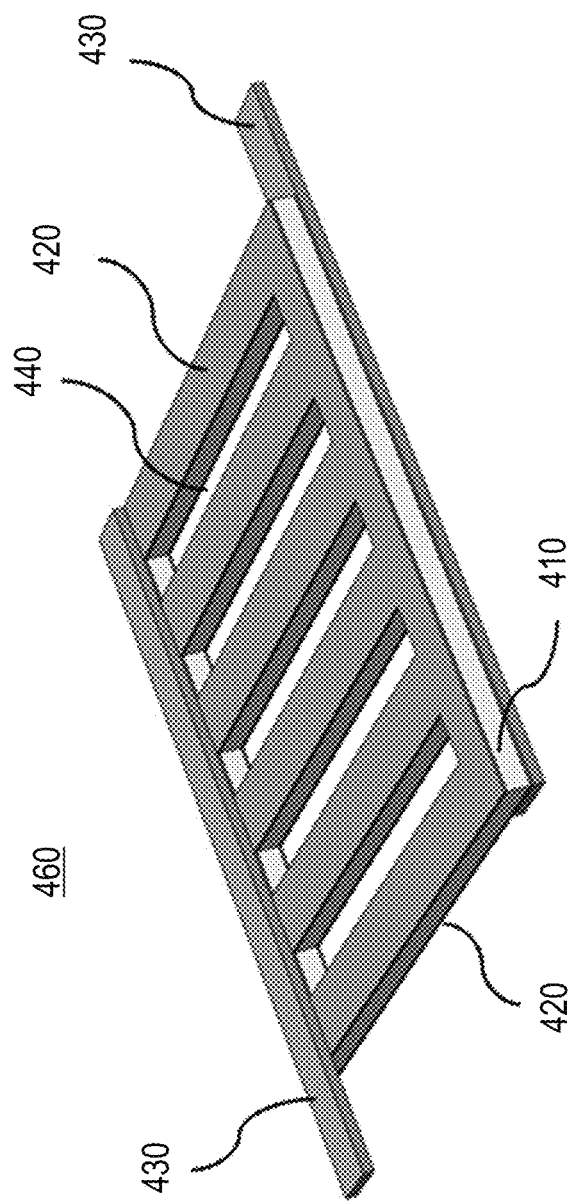
FIG. 4 illustrates an example positive temperature coefficient of resistivity heater that includes positive temperature coefficient of resistivity material sandwiched between electrically conductive layers, consistent with implementations of the current subject matter.

A PTCR heater can be formed in any number of geometries. For example, FIG. 4 illustrates an example PTCR heater 460 that includes PTCR material 410 sandwiched between electrically conductive layers 420. The PTCR material 410 includes rectangular holes 440. Electrically conductive layers 420 are attached to conductive leads 430 such that conductive leads 430 may have differential voltage applied. The rectangular holes 440 provide paths for vapor to escape in one instance where PTCR heater 460 is in contact with material pre-saturated with liquid to be vaporized.

Hole shapes and sizes in PTCR heater 460 can be any size, spacing and shape, where said shape may include any polygon or circle, which can be configured for vaporization.

Figure 5:
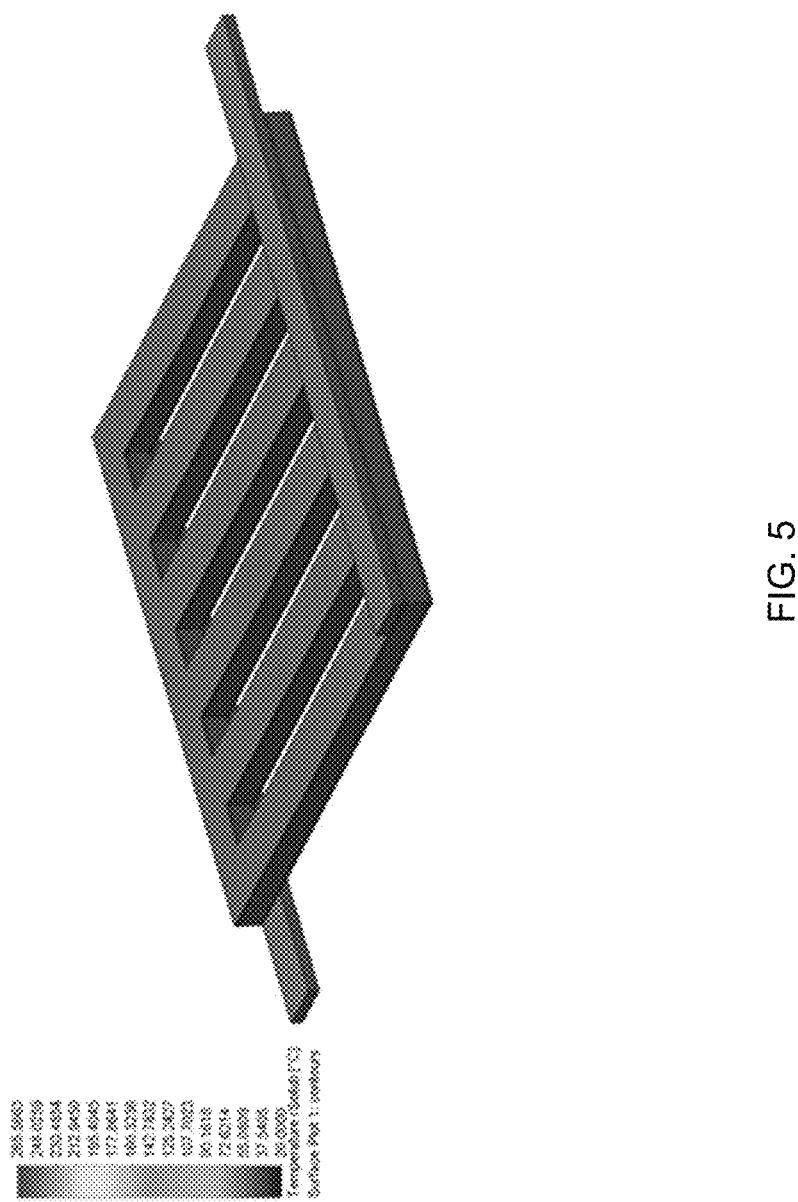
FIG. 5 illustrates temperature for the example heater of FIG. 4, consistent with implementations of the current subject matter.

FIG. 5 illustrates temperature for the example PTCR heater 460 modeled with applied voltage, temperatures after 2.0 seconds show temperatures of 265±1.0° C. as shown in FIG. 5.

Figure 6:
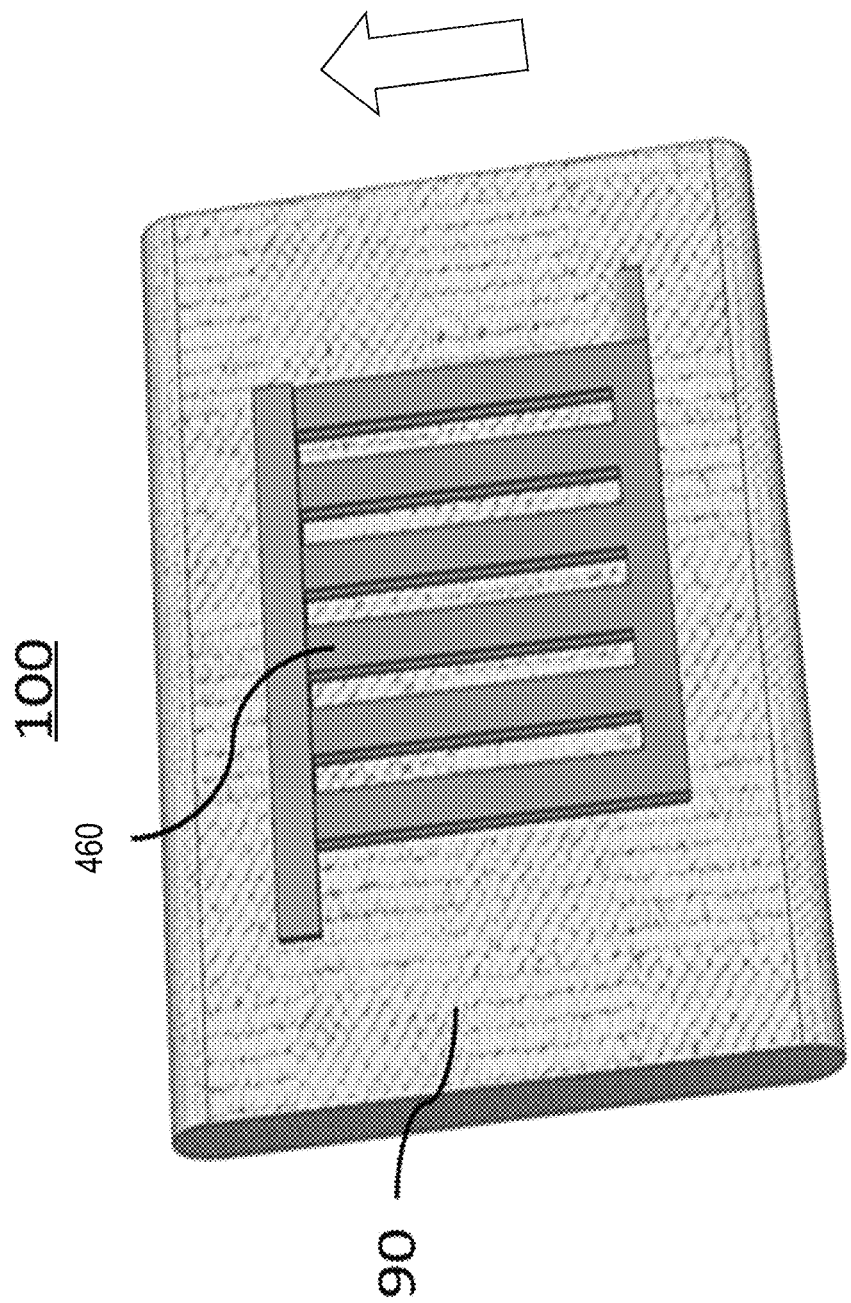
FIG. 6 illustrates an example vaporizing assembly that includes a fibrous wick with attached example heater mounted on one flat side of the fibrous wick, consistent with implementations of the current subject matter.

FIG. 6 illustrates an example vaporizing assembly 100 that includes a fibrous wick 90 with attached example PTCR heater 460 mounted on one flat side of the fibrous wick 90 (e.g., a wide surface of the wick 90). In some implementations, a PTCR heater 460 can be mounted on both flat sides of fibrous wick 90. In some implementations, the vaporizing assembly 100 can be arranged within a vaporizing device such that inflow of air (typically generated by the user of a vaporizer device) can be directed parallel to the broad side of vaporizing assembly 100, as illustrated by the arrow. Such a construct of vaporizing assembly with directed airflow can ensure that vapor will be generated primarily at areas heated by PTCR heater 460. Parallel airflow can generate appropriate (e.g., maximum) surface shear stress at the area of the primary vapor generation, thereby improving vaporization device operation.

Figure 7:
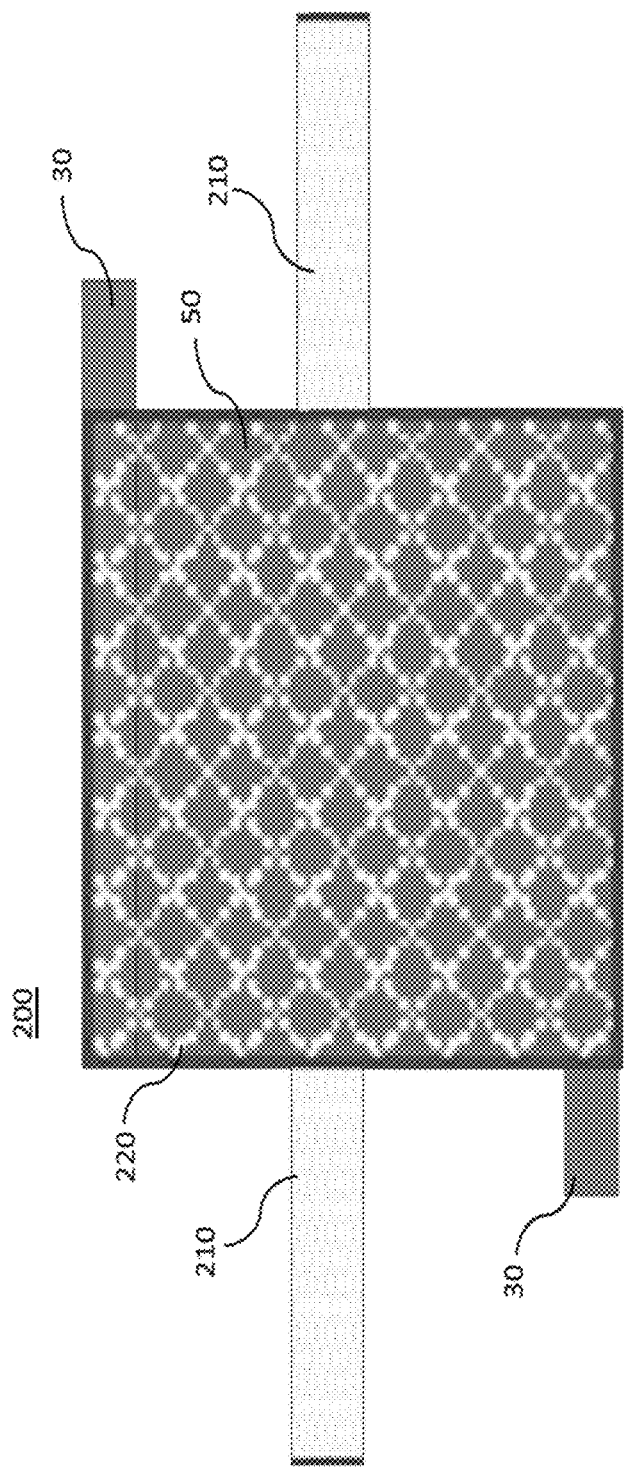
FIG. 7 illustrates another example implementation of a vaporizing assembly with heater surrounded by open weave wicking material, consistent with implementations of the current subject matter.

FIG. 7 illustrates another example implementation of a vaporizing assembly 200 with PTCR heating element 50 having conductive leads 30 surrounded by open weave wicking material 220 such that the ends of the open weave wicking material 220 are wound into a cylinder shape 210 for receiving a vaporizable material (not shown). The example arrangement in FIG. 7 enables the wick ends to be smaller than the PTCR heating element, while still utilizing the larger PTCR heating element surface area for improved heating. Other constructs of the vaporizing assembly are possible.

Figure 8:
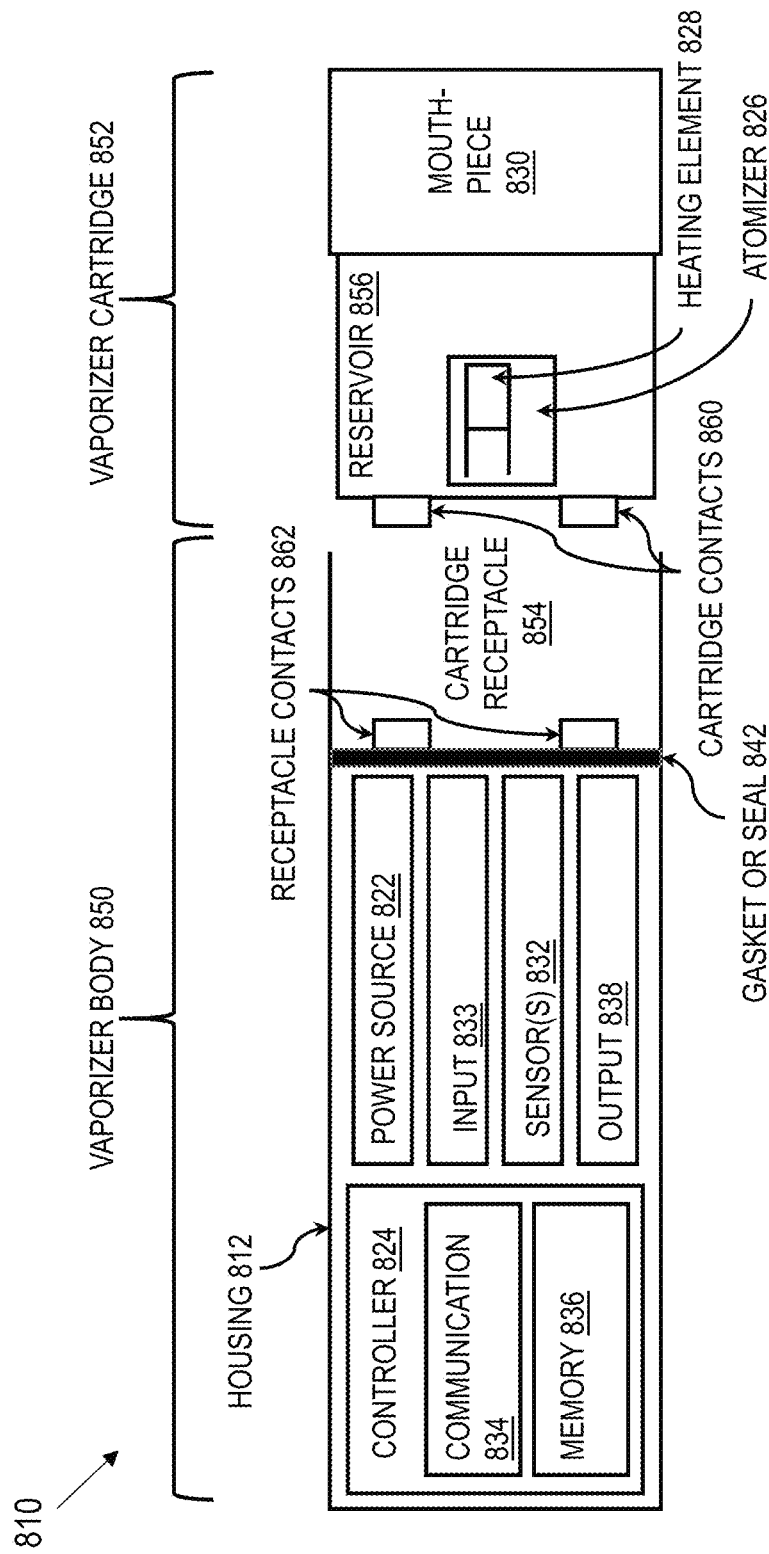
FIG. 8 is a block diagram illustrating an example vaporizer, consistent with implementations of the current subject matter.

A PTCR heating element can be implemented in a vaporizer device. Referring to the block diagram of FIG. 8, an example vaporizer 810 includes a housing 812 containing a power source 822 (such as a battery which may be a rechargeable battery) to provide a current flow at a voltage, and optionally a controller 824 (e.g., a processor, circuitry, etc., capable of executing logic) for controlling delivery of heat to an atomizer 826 to cause a vaporizable material to be converted from a condensed form (e.g., a solid, a liquid, a solution, a suspension, a part of an at least partially unprocessed plant material, etc.) to the gas phase. The optional controller 824 may be part of one or more printed circuit boards (PCBs) consistent with certain implementations of the current subject matter. Atomizer 826 includes a wicking element (also referred to herein as a wicking element (not shown in FIG. 8), and a PTCR heating element 828. The wicking element may allow air to enter the reservoir to replace the volume of liquid removed. In other words, capillary action pulls liquid vaporizable material into the wicking element for vaporization by the PTCR heating element (described below), and air may, in some implementations of the current subject matter, return to the reservoir through the wicking element to at least partially equalize pressure in the reservoir. Other approaches to allowing air back into the reservoir to equalize pressure are also within the scope of the current subject matter.

The PTCR heating element 828 includes a PTCR material. In some implementations, the PTCR heating element can be or include one or more of a conductive heater, a radiative heater, and a convective heater. In some implementations of the current subject matter, an atomizer can include a PTCR heating element that can be wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed herein.

Certain vaporizers may also or alternatively be configured to create an inhalable dose of gas-phase and/or aerosol-phase vaporizable material via heating of a non-liquid vaporizable material, such as for example a solid-phase vaporizable material (e.g., a wax or the like) or plant material (e.g., tobacco leaves and/or parts of tobacco leaves) containing the vaporizable material. In such vaporizers, a PTCR heating element may be part of or otherwise incorporated into or in thermal contact with the walls of an oven or other heating chamber into which the non-liquid vaporizable material is placed. Alternatively, a PTCR heating element or elements may be used to heat air passing through or past the non-liquid vaporizable material to cause convective heating of the non-liquid vaporizable material. In still other examples, a PTCR heating element or elements may be disposed in intimate contact with plant material such that direct conductive heating of the plant material occurs from within a mass of the plant material (e.g., as opposed to only by conduction inward form walls of an oven).

The PTCR heating element may be activated (e.g., by a controller, which can be part of a vaporizer body as discussed below, and which may cause current to pass from the power source through a circuit including the PTCR heating element, which can be part of a vaporizer cartridge as discussed below) in association with a user puffing (e.g., drawing, inhaling, and the like) on a mouthpiece 830 of the vaporizer to cause air to flow from an air inlet, along an airflow path that passes an atomizer 826 (e.g., wicking element and PTCR heating element 828), which in some implementations can be through one or more condensation areas or chambers, to an air outlet in the mouthpiece. Incoming air passing along the airflow path passes over, through, and the like, the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 830 for inhalation by a user).

Activation of the PTCR heating element 828 is caused by closing a circuit between the power source and the PTCR heating element using an input device 833. In some implementations, the input device 833 is a switch may be used to electrically complete a circuit between the power source and the PTCR heating element. In some implementations, the input device 833 includes a relay, a solenoid, and/or a solid-state device that may be used to electrically complete a circuit between the power source and the PTCR heating element.

Activation of the PTCR heating element 828 may optionally be caused by automatic detection of the puff based on one or more of signals generated by one or more sensors 832, such as for example a pressure sensor or sensors disposed to detect pressure along the airflow path relative to ambient pressure (or optionally to measure changes in absolute pressure), one or more motion sensors of the vaporizer 810, one or more flow sensors of the vaporizer 810, a capacitive lip sensor of the vaporizer 810; in response to detection of interaction of a user with one or more input devices 833 (e.g., buttons or other tactile control devices of the vaporizer 810), receipt of signals from a computing device in communication with the vaporizer 810; and/or via other approaches for determining that a puff is occurring or imminent.

As alluded to in the previous paragraph, a vaporizer consistent with implementations of the current subject matter may optionally be configured to connect (e.g., wirelessly or via a wired connection) to a computing device (or optionally two or more devices) in communication with the vaporizer 810. To this end, the optional controller 824 may include communication hardware 834. The optional controller 824 may also include a memory 836. A computing device can be a component of a vaporizer system that also includes the vaporizer 810, and can include its own communication hardware, which can establish a wireless communication channel with the communication hardware 834 of the vaporizer 810. For example, a computing device used as part of a vaporizer system may include a general purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer 810 can also include one or more output 838 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, and the like), controlling nicotine delivery (e.g., switching between nicotine and non-nicotine vaporizable material, adjusting an amount of nicotine delivered, and the like), obtaining locational information (e.g., location of other users, retailer/commercial venue locations, vaping locations, relative or absolute location of the vaporizer itself, and the like), vaporizer personalization (e.g., naming the vaporizer, locking/password protecting the vaporizer, adjusting one or more parental controls, associating the vaporizer with a user group, registering the vaporizer with a manufacturer or warranty maintenance organization, and the like), engaging in social activities (e.g., games, social media communications, interacting with one or more groups, and the like) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the PTCR heating element, or in other examples of coupling of a computing device with a vaporizer for implementation of various control or other functions, the computing device executes one or more computer instruction sets to provide a user interface and underlying data handling. In one example, detection by the computing device of user interaction with one or more user interface elements can cause the computing device to signal the vaporizer 810 to activate the PTCR heating element 828 to a full operating temperature for creation of an inhalable dose of vapor/aerosol. Other functions of the vaporizer 810 may be controlled by interaction of a user with a user interface on a computing device in communication with the vaporizer.

The temperature of a PTCR heating element of a vaporizer may depend on a number of factors, including conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the PTCR heating element or the atomizer as a whole when a user inhales on the electronic vaporizer). As noted above, to reliably activate the PTCR heating element or heat the PTCR heating element to a desired temperature, a vaporizer may, in some implementations of the current subject matter, make use of signals from a pressure sensor to determine when a user is inhaling. The optional pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the PTCR heating element may be activated in association with a user's puff, for example by automatic detection of the puff, for example by the pressure sensor detecting a pressure change in the airflow path.

Typically, the optional pressure sensor (as well as any other sensors 832) can be positioned on or coupled (e.g., electrically or electronically connected, either physically or via a wireless connection) to the optional controller 824 (e.g., a printed circuit board assembly or other type of circuit board). To take measurements accurately and maintain durability of the vaporizer, it can be beneficial to provide an optional resilient seal 842 to separate an airflow path from other parts of the vaporizer 810. The optional seal 842, which can be a gasket, may be configured to at least partially surround the optional pressure sensor such that connections of the optional pressure sensor to internal circuitry of the vaporizer 810 are separated from a part of the optional pressure sensor exposed to the airflow path. In an example of a cartridge-based vaporizer, the optional seal or gasket 842 may also separate parts of one or more electrical connections between a vaporizer body 850 and a vaporizer cartridge 852. Such arrangements of an optional gasket or seal 842 in a vaporizer 810 can be helpful in mitigating against potentially disruptive impacts on vaporizer components resulting from interactions with environmental factors such as water in the vapor or liquid phases, other fluids such as the vaporizable material, etc., and/or to reduce escape of air from the designed airflow path in the vaporizer 810. Unwanted air, liquid or other fluid passing and/or contacting circuitry of the vaporizer can cause various unwanted effects, such as alter pressure readings, and/or can result in the buildup of unwanted material, such as moisture, the vaporizable material, etc., in parts of the vaporizer 810 where they may result in poor pressure signal, degradation of the pressure sensor or other components, and/or a shorter life of the vaporizer 810. Leaks in the optional seal or gasket 842 can also result in a user inhaling air that has passed over parts of the vaporizer device 810 containing or constructed of materials that may not be desirable to be inhaled.

A general class of vaporizers that have recently gained popularity includes a vaporizer body 850 that includes an optional controller 824, a power source 822 (e.g., battery), one more optional sensors 832, charging contacts, an optional gasket or seal 842, and a cartridge receptacle 854 configured to receive a vaporizer cartridge 852 for coupling with the vaporizer body 850 through one or more of a variety of attachment structures. In some examples, vaporizer cartridge 852 includes a reservoir 856 including an inlet (not shown) for receiving a liquid vaporizable material and an outlet (not shown) for releasing a the vaporized material, and a mouthpiece 830 for delivering an inhalable dose of the vaporized material to a user. The vaporizer cartridge 852 can include an atomizer 826 having a wicking element and a PTCR heating element 828, or alternatively, one or both of the wicking element and the PTCR heating element 828 can be part of the vaporizer body 850. In implementations in which any part of the atomizer 826 (e.g., heating element 828 and/or wicking element) is part of the vaporizer body 850, the vaporizer 810 can be configured to supply liquid vaporizer material from a reservoir 856 in the vaporizer cartridge 852 to the atomizer 826 part(s) included in the vaporizer body 850.

Cartridge-based configurations for vaporizers that generate an inhalable dose of a non-liquid vaporizable material via heating of a non-liquid vaporizable material are also within the scope of the current subject matter. For example, a vaporizer cartridge may include a mass of a plant material that is processed and formed to have direct contact with parts of one or more PTCR heating elements, and such a vaporizer cartridge may be configured to be coupled mechanically and electrically to a vaporizer body that includes a processor, a power source, and electrical contacts for connecting to corresponding cartridge contacts for completing a circuit with the one or more PTCR heating elements.

In vaporizers in which the power source 822 is part of a vaporizer body 850 and a PTCR heating element 828 is disposed in a vaporizer cartridge 852 configured to couple with the vaporizer body 850, the vaporizer 810 may include electrical connection features (e.g., means for completing a circuit) for completing a circuit that includes the optional controller 824 (e.g., a printed circuit board, a microcontroller, or the like), the power source 822, and the PTCR heating element 828. These features may include at least two contacts on a bottom surface of the vaporizer cartridge 852 (referred to herein as cartridge contacts 860) and at least two contacts disposed near a base of the cartridge receptacle (referred to herein as receptacle contacts 862) of the vaporizer 810 such that the cartridge contacts 860 and the receptacle contacts 862 make electrical connections when the vaporizer cartridge 852 is inserted into and coupled with the cartridge receptacle 854. The circuit completed by these electrical connections can allow delivery of electrical current to the PTCR heating element 828 and may further be used for additional functions, such as for example, for identifying a cartridge based on one or more electrical characteristics of a PTCR heating element 828 or the other circuitry of the vaporizer cartridge 852, and the like.

In some examples of the current subject matter, the at least two cartridge contacts 860 and the at least two receptacle contacts 862 can be configured to electrically connect in either of at least two orientations. In other words, one or more circuits necessary for operation of the vaporizer 810 can be completed by insertion of a vaporizer cartridge 852 in the cartridge receptacle 854 in a first rotational orientation (around an axis along which the end of the vaporizer cartridge 852 having the cartridge is inserted into the cartridge receptacle 854 of the vaporizer body 850) such that a first cartridge contact of the at least two cartridge contacts 860 is electrically connected to a first receptacle contact of the at least two receptacle contacts 862 and a second cartridge contact of the at least two cartridge contacts 860 is electrically connected to a second receptacle contact of the at least two receptacle contacts 862. Furthermore, the one or more circuits necessary for operation of the vaporizer can be completed by insertion of a vaporizer cartridge 852 in the cartridge receptacle 854 in a second rotational orientation such that the first cartridge contact of the at least two cartridge contacts 860 is electrically connected to the second receptacle contact of the at least two receptacle contacts 862 and the second cartridge contact of the at least two cartridge contacts 860 is electrically connected to the first receptacle contact of the at least two receptacle contacts 862. This feature of a vaporizer cartridge 852 being reversibly insertable into a cartridge receptacle 854 of the vaporizer body 850 is described further below.

The at least two cartridge contacts 860 and the at least two receptacle contacts 862 can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge 852 and the vaporizer body 850. The electrical contacts may optionally be gold-plated, and/or can include other materials.

Figure 9:
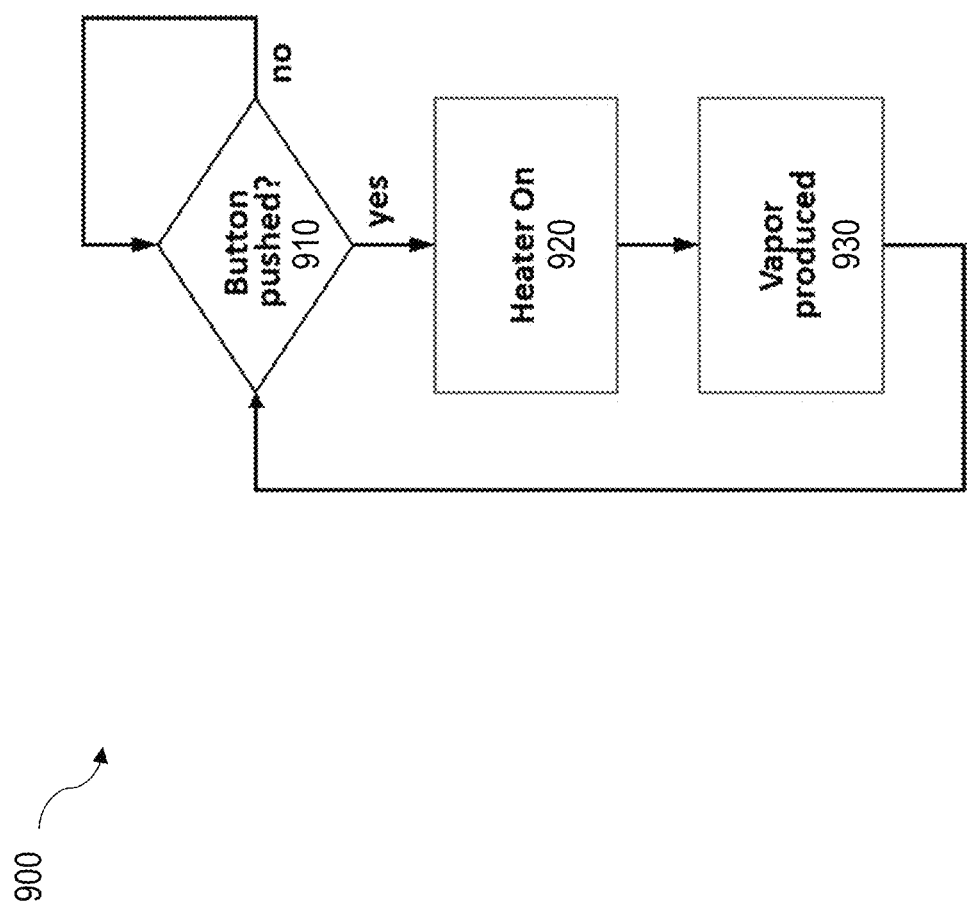
FIG. 9 illustrates a process flow chart of an example process of operating an example vaporizer device utilizing a positive temperature coefficient of resistivity heating element, consistent with implementations of the current subject matter.

FIG. 9 is a process flow chart illustrating an example process 900 of operating an example vaporizer device utilizing a PTCR heating element. Because the vaporizer utilizes a PTCR heating element, temperature control can be intrinsic such that feedback temperature sensors and power duty cycling may not be required and more uniform heating can be achieved.

At 910, the vaporizer (e.g., controller) can determine whether an input has been provided by a user. The input can be to a pushbutton, via a pressure sensor sensing an inhale, and the like. The input can include an open pushbutton or other means that completes a circuit between a battery and a PTCR heater. If the input has not been provided at 910, the process waits until an input is provided. When the input is provided, the process proceeds to step 920.

At 920, the electrical circuit connecting the PTCR heating element to the power source is in a closed state such that current flows to the PTCR heating element. The PTCR heating element increases in temperature as a result of the current flow. Once the temperature of the PTCR heating element reaches the electrical resistivity transition zone, the resistivity of the PTCR heating element increases until current flow is reduced and an equilibrium is reached such that the PTCR heating element maintains a uniform temperature without active control by the vaporizer (e.g., the temperature will maintain at a value based on the material properties of the PTCR heating element). In other words, the vaporizer controller does not have to perform any temperature sensing or duty cycle the power source in order to maintain the desired temperature. Accordingly, when using a PTCR heating element, heating and self-regulating at a desired temperature is achieved. In some implementations, the pushbutton may be replaced with a mechanical switch triggered by a snap-through threshold pressure valve with hysteresis, or by other means.

At 930, vapor is produced because of the heating. By utilizing a PTCR heating element with intrinsic temperature control, overheating (e.g., burning) of the vaporizer fluid (or other material) can be avoided, thereby avoiding formation of unwanted, and potentially dangerous, chemical byproducts.

FIG. 10A-FIG. 10F illustrate modeled temperatures of another example of a PTCR heating element 50. A gradient temperature scale is shown on the left side of each figure with red representing the hottest temperature of about 255° C. and continues through the colors of the visible light spectrum in order (i.e. red, orange, yellow, green, blue, and violet) to the coolest temperature of about 23° C. In each of the illustrated examples, the nonlinear PTCR material 10 includes a plate geometry with dimensions of about 5 mm×5 mm×0.5 mm; the conductive layers 20 were formed of silver (Ag) with dimensions of about 5 mm×5 mm×0.025 mm; and the conductive leads 30 were formed of copper (CU) with dimensions of about 12 mm×2 mm×0.2 mm. The plate geometry can include two parallel sides including conductive layers 20 with conductive leads 30 attached thereto. The conductive leads 30 are centrally attached to conductive layers 20 on each side of the PTCR heating element 50 with a connection 40. In some implementations, the connection 40 is a clamp, a clip, a conductive paste, a high-temperature, lead-free solder, and/or combinations thereof.

Figure 10A:
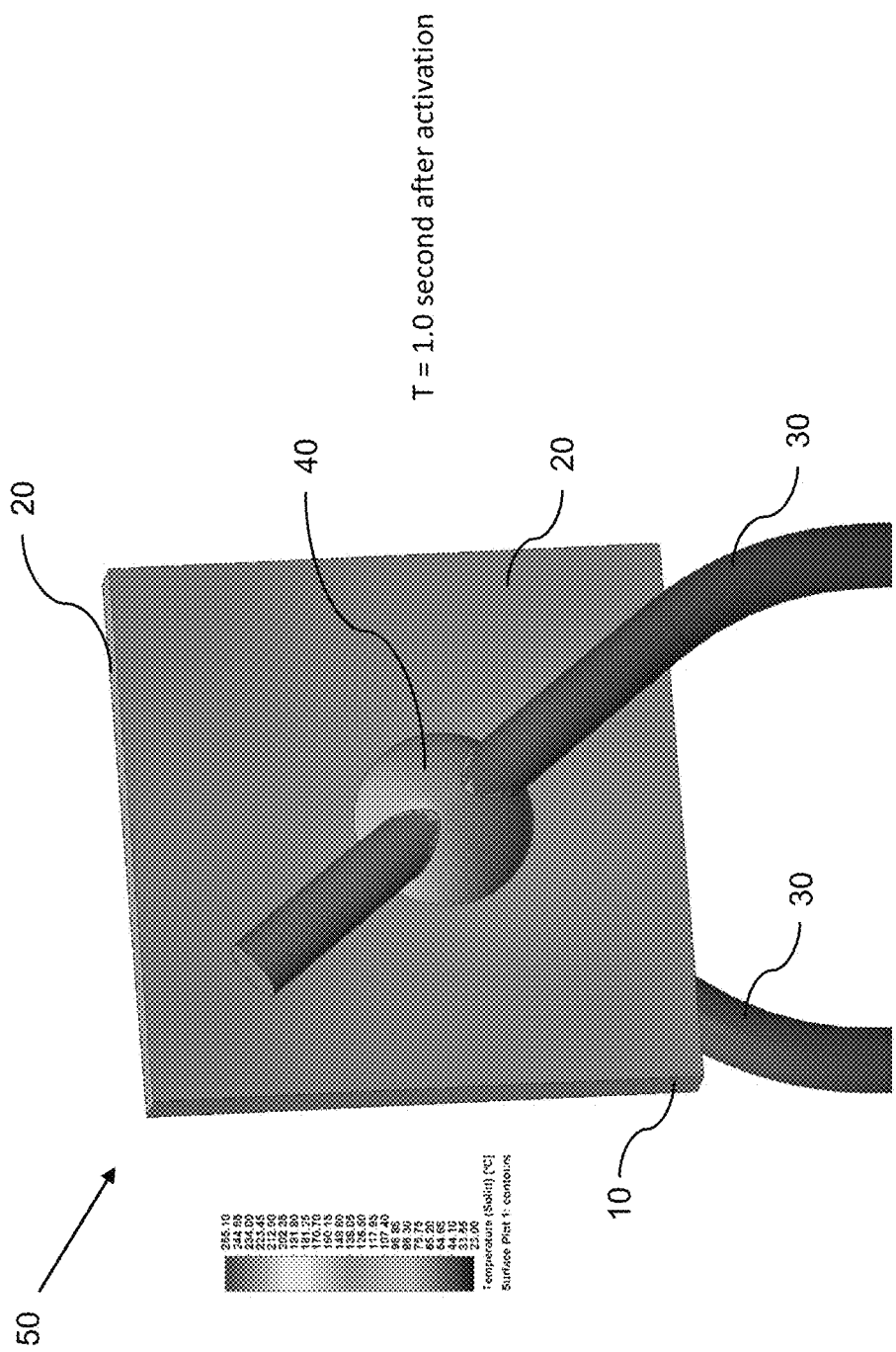
FIG. 10A-FIG. 10F illustrate modeled temperatures of an example PTCR heater, consistent with implementations of the current subject matter.

FIG. 10A illustrates the temperature 1.0 second after activation by applying a current to the PTCR heating element 50. The violet colored conductive leads 30 are still about 25° C. The majority of the PTCR material 10 and conductive layer 20 has increased in temperature to about 120° C., with the area including connection 40 in the center being slightly cooler at a temperature around 80° C.

Figure 10B:
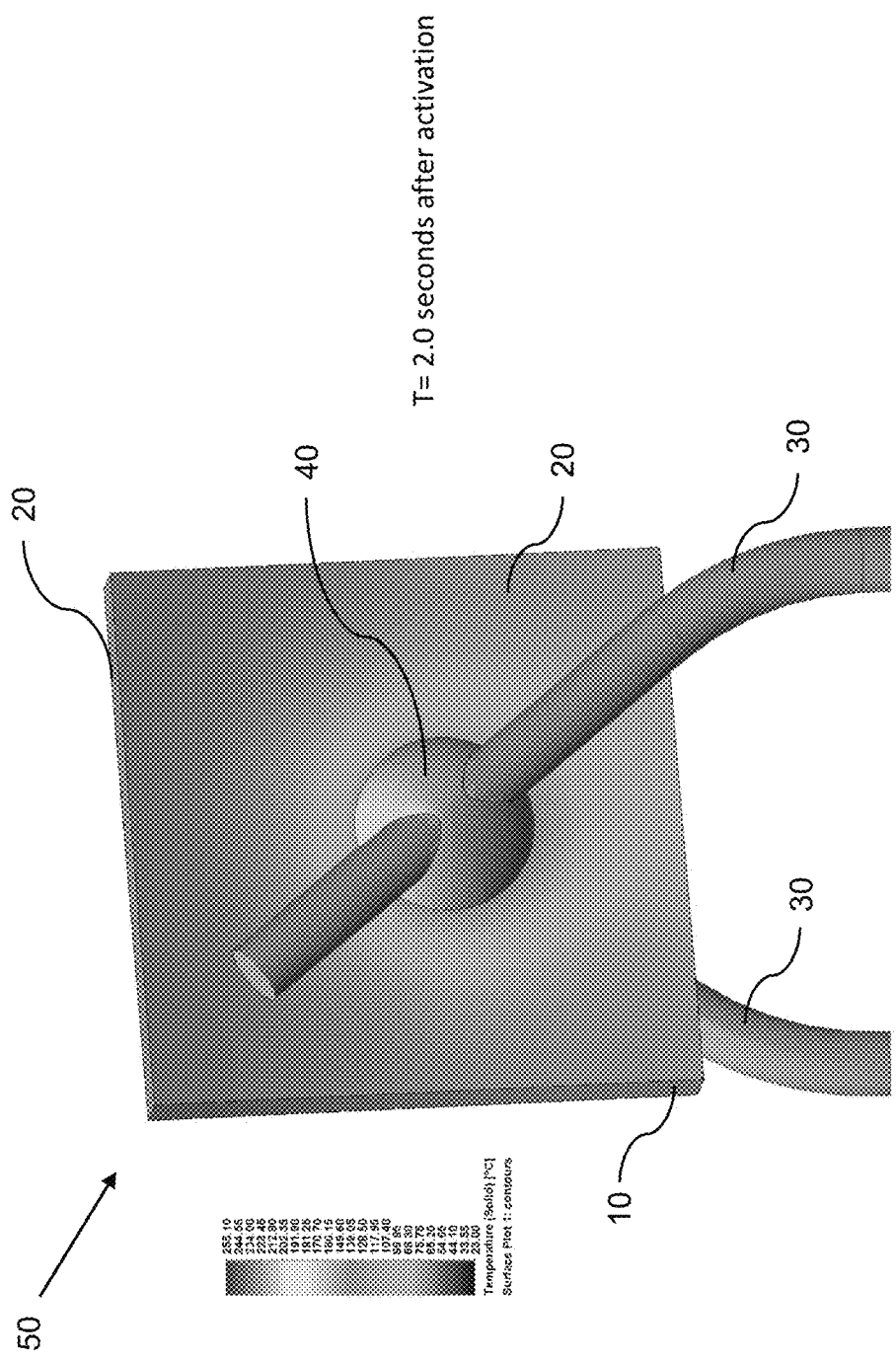

FIG. 10B illustrates the temperature 2.0 seconds after activation by applying a current to the PTCR heating element 50. The blue/green colored conductive leads 30 have increased in temperature to about 90° C. The majority of the PTCR material 10 and conductive layer 20 has increased in temperature to about 210° C., with the area including connection 40 in the center being cooler at a temperature around 160° C.

Figure 10C:
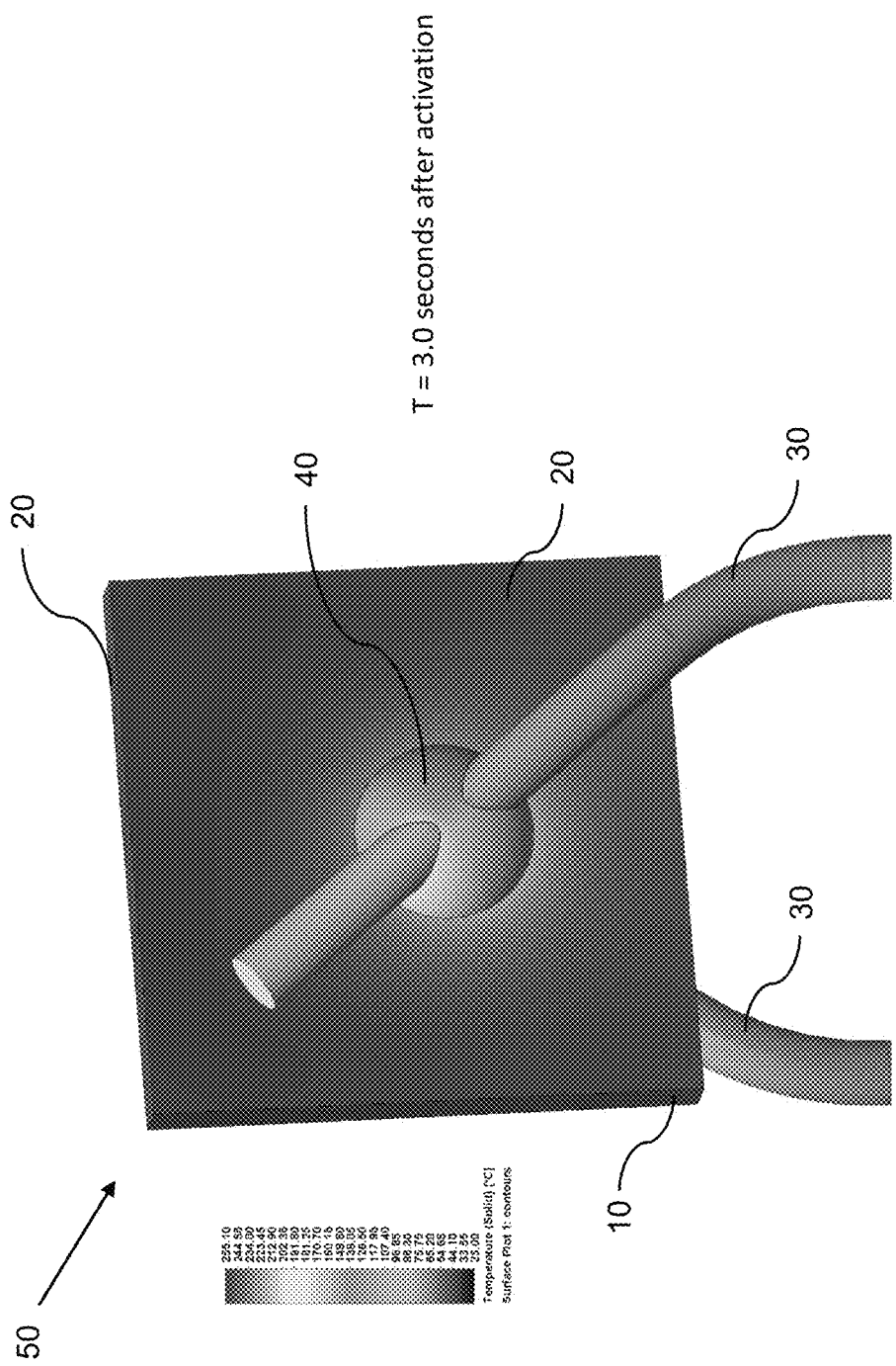

FIG. 10C illustrates the temperature 3.0 seconds after activation by applying a current to the PTCR heating element 50. The green colored conductive leads 30 have increased in temperature to about 140° C. The majority of the PTCR material 10 and conductive layer 20 has increased in temperature to about 250° C., with the area including connection 40 in the center being cooler at a temperature around 200° C.

Figure 10D:
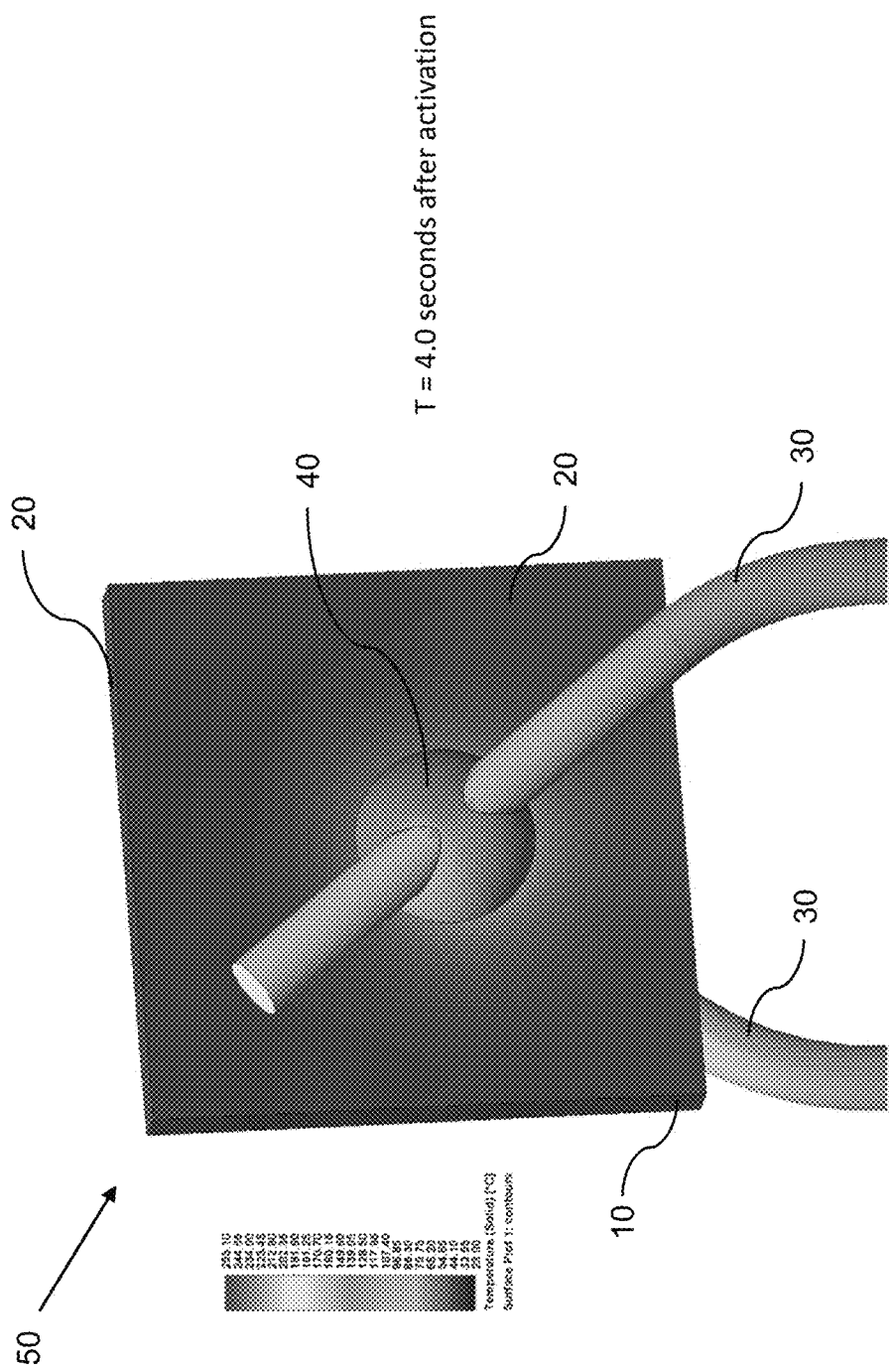

FIG. 10D illustrates the temperature 4.0 seconds after activation by applying a current to the PTCR heating element 50. The green colored conductive leads 30 have increased in temperature to about 160° C. The majority of the PTCR material 10 and conductive layer 20 remains at temperature to about 250° C., with the area including connection 40 in the center being cooler at a temperature around 215° C.

Figure 10E:
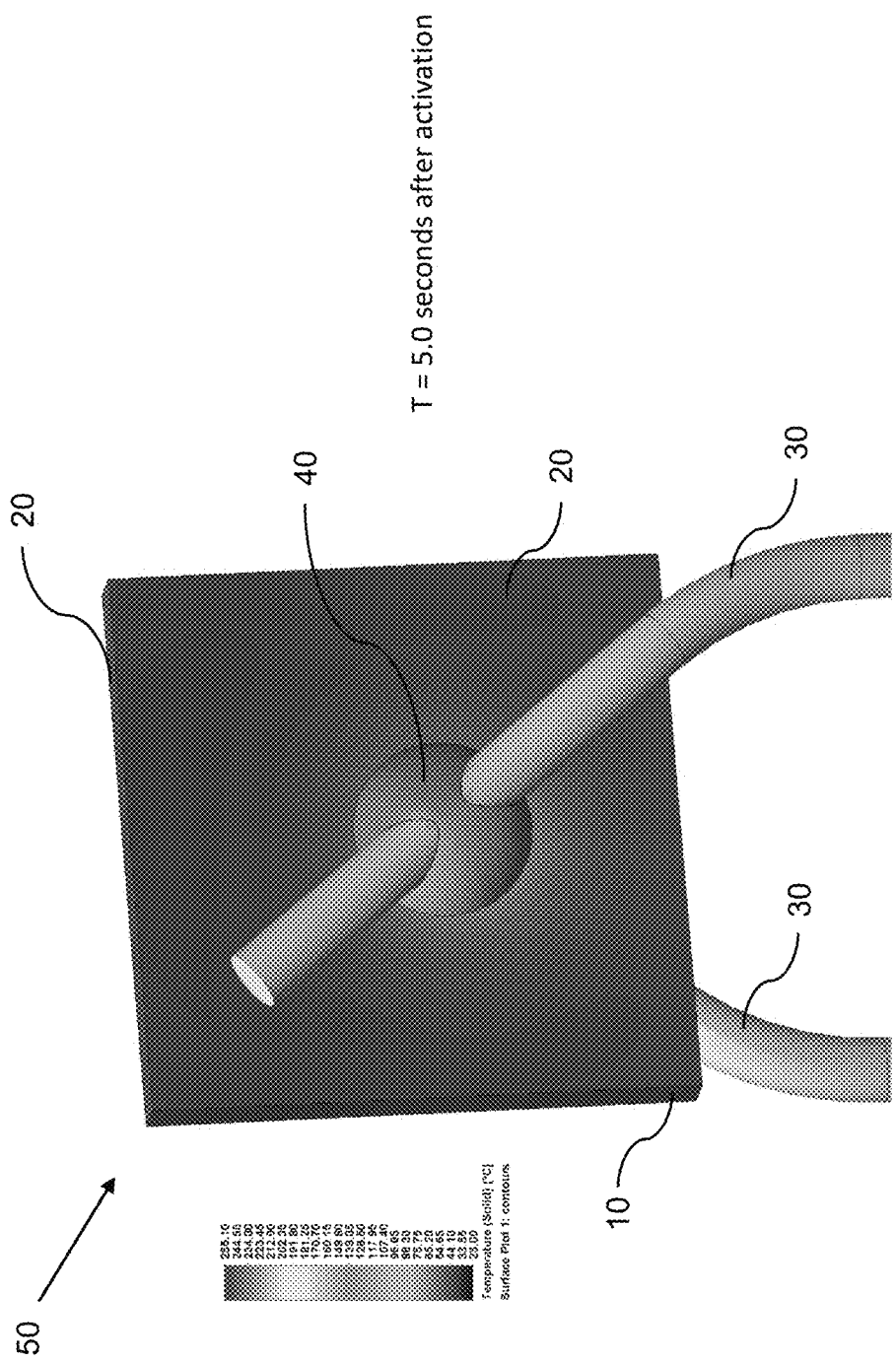

FIG. 10E illustrates the temperature 5.0 seconds after activation by applying a current to the PTCR heater 50. The green/yellow colored conductive leads 30 have increased in temperature to about 180° C. The majority of the PTCR material 10 and conductive layer 20 remains at temperature to about 250° C., with the area including connection 40 in the center being slightly cooler at a temperature around 225° C.

Figure 10F:
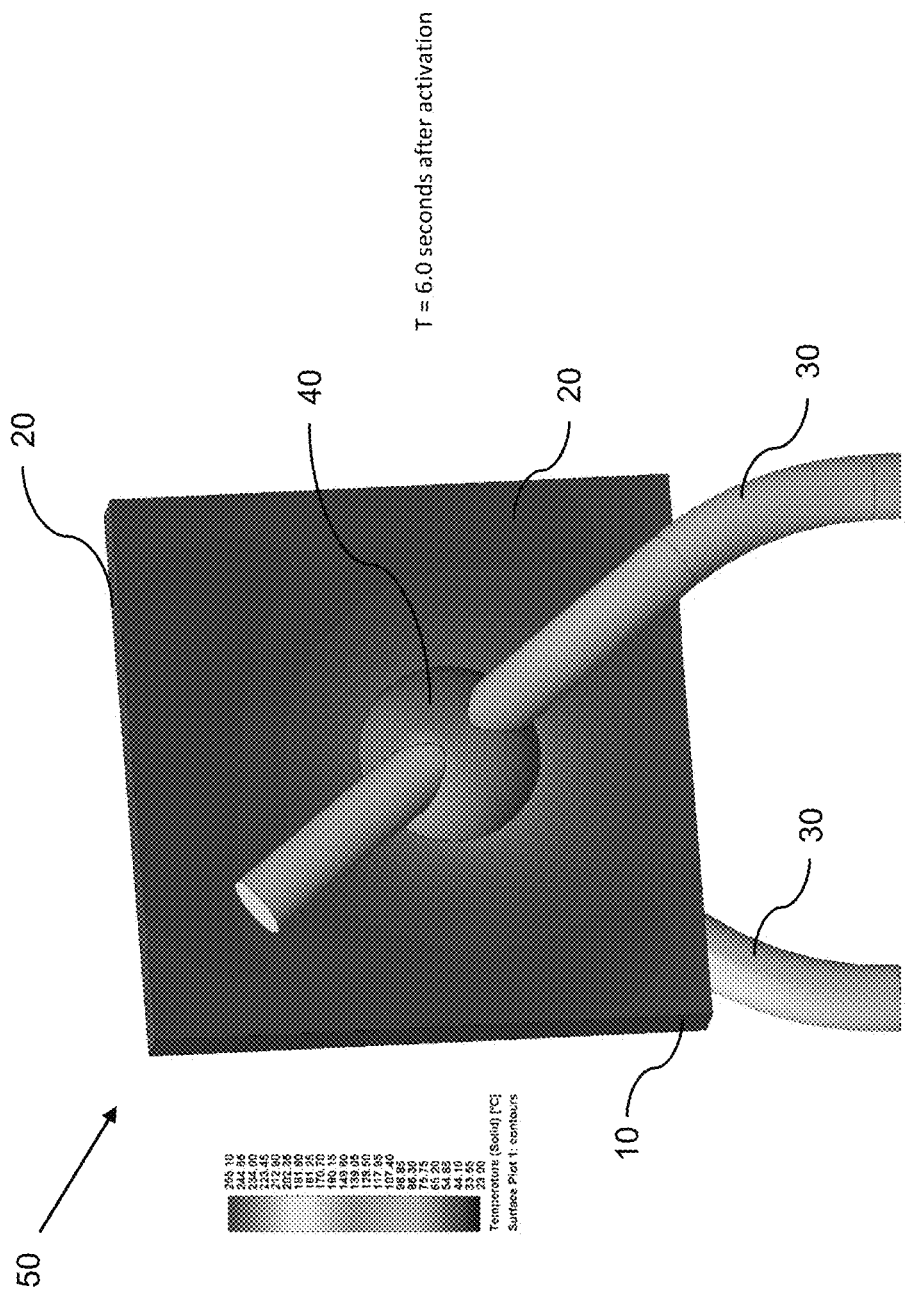

FIG. 10F illustrates the temperature 6.0 seconds after activation by applying a current to the PTCR heating element 50. The yellow colored conductive leads 30 have increased in temperature to about 200° C. The majority of the PTCR material 10 and conductive layer 20 remains at temperature to about 250° C., with the area including connection 40 in the center being just slightly cooler at a temperature around 235° C.

Figure 11A:
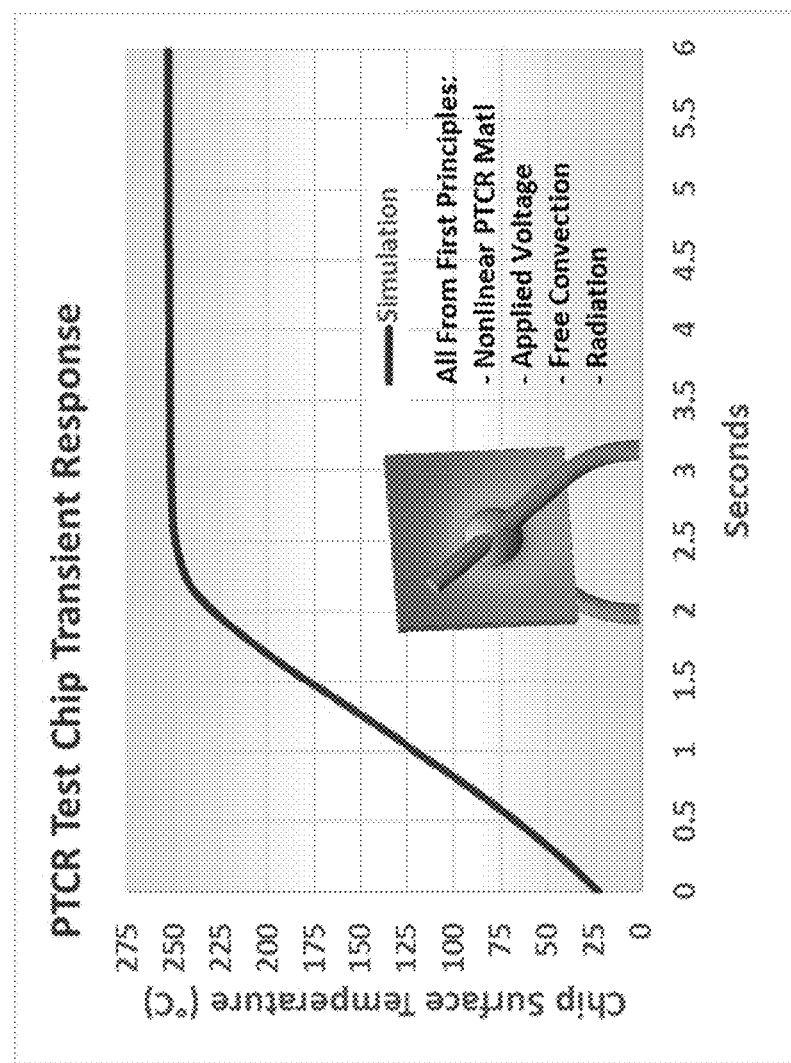
FIG. 11A illustrates a modeled surface temperature as a function of time for an example PTCR heater, consistent with implementations of the current subject matter.

FIG. 11A illustrates a modeled surface temperature as a function of time for an example PTCR heating element. In the model, the surface temperature of the PTCR heater starts at 25° C. (i.e. room temperature) at time zero. After an electrical current is applied, the surface temperature increases linearly for about 2 seconds to a temperature of about 225° C. After about 2 seconds, the rate of the temperature increase tapers off to a steady-state operating temperature of about 250° C. that is achieve about 3 seconds after activation. In the model, it was assumed that the nonlinear PTCR material is in a non-contact, free convective state, and the emitted radiation was measured from a distance. In some implementations, the PTCR heating element is heated to an operating temperature between 240° C. and 280° C. In some implementations, the PTCR heating element is heated to an operating temperature between 245° C. and 255° C. In some implementations, the PTCR heating element is heated to an operating temperature about 250° C.

Figure 11B:
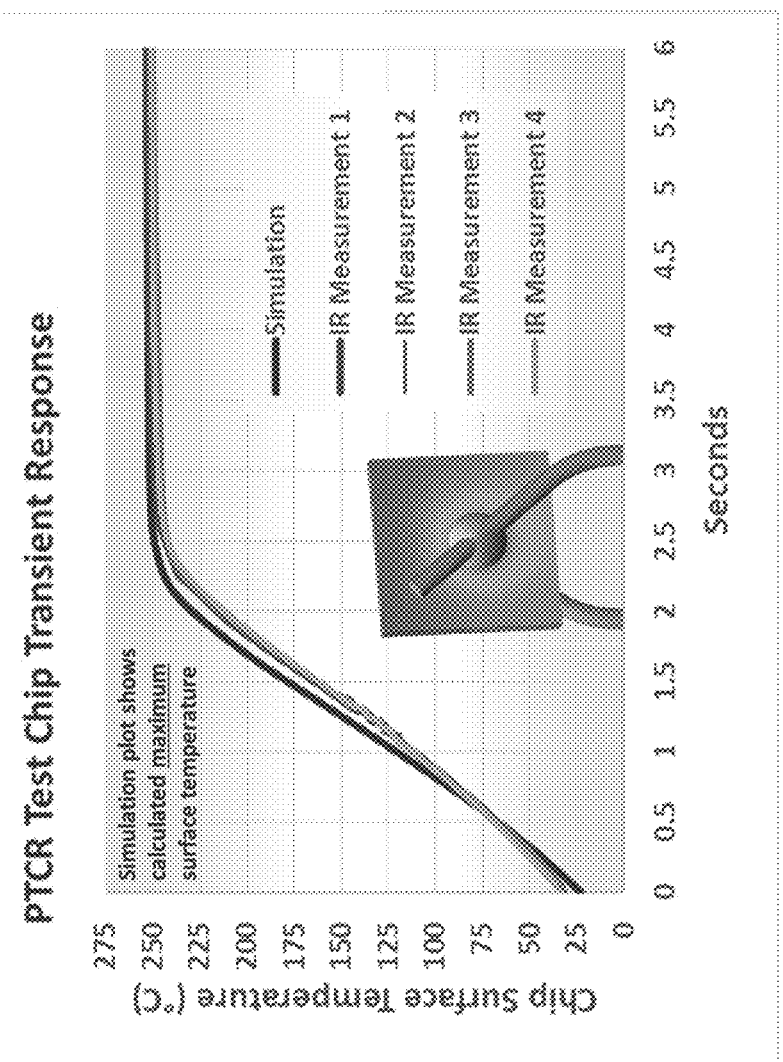
FIG. 11B illustrates a modeled and measured maximum surface temperatures as a function of time of an example PTCR heater, consistent with implementations of the current subject matter.

FIG. 11B illustrates a modeled and measured maximum surface temperatures as a function of time for an example PTCR heater. Four measurements were repeated using an infrared camera to measure the maximum surface temperatures of the PTCR heater as a function of time, which were then plotted against the model of the maximum surface temperature. In the model, it was assumed that the nonlinear PTCR material is in a non-contact, free convective state and the emitted radiation was measured from a distance. In each case, the maximum surface temperature of the PTCR heating element starts at about 25° C. (i.e. room temperature) at time zero. After an electrical current is applied, the maximum surface temperature increases linearly for about 2 seconds to a temperature of about 225° C. After about 2 seconds, the rate of the temperature increase tapers off to a steady-state operating temperature of about 250° C. that is achieve about 3 seconds after activation. In some implementations, the PTCR heating element is heated to an operating temperature between 240° C. and 280° C. In some implementations, the PTCR heating element is heated to an operating temperature between 245° C. and 255° C. In some implementations, the PTCR heating element is heated to an operating temperature about 250° C.

Figure 11C:
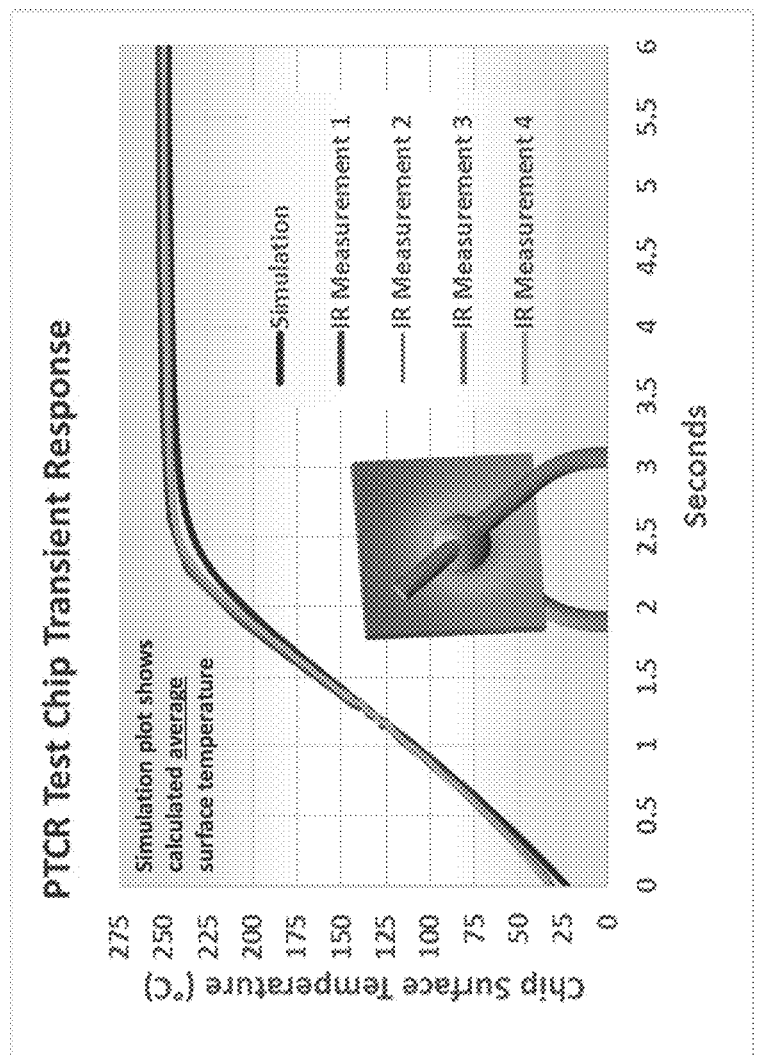
FIG. 11C illustrates a modeled and measured average surface temperatures as a function of time of an example PTCR heater, consistent with implementations of the current subject matter.

FIG. 11C illustrates a modeled and measured average surface temperatures as a function of time for an example PTCR heating element. Four measurements were repeated using an infrared camera to measure the average surface temperatures of the PTCR heating element as a function of time, which were then plotted against the model of the average surface temperature. In the model, it was assumed that the nonlinear PTCR material is in a non-contact, free convective state and the emitted radiation was measured from a distance. In each case, the average surface temperature of the PTCR heating element starts at about 25° C. (i.e. room temperature) at time zero. After an electrical current is applied, the maximum surface temperature increases linearly for about 2 seconds to a temperature of about 225° C. After about 2 seconds, the rate of the temperature increase tapers off to a steady-state operating temperature of about 250° C. that is achieve about 3 seconds after activation. In some implementations, the PTCR heating element is heated to an operating temperature between 240° C. and 280° C. In some implementations, the PTCR heating element is heated to an operating temperature between 245° C. and 255° C. In some implementations, the PTCR heating element is heated to an operating temperature about 250° C.

Figure 12:
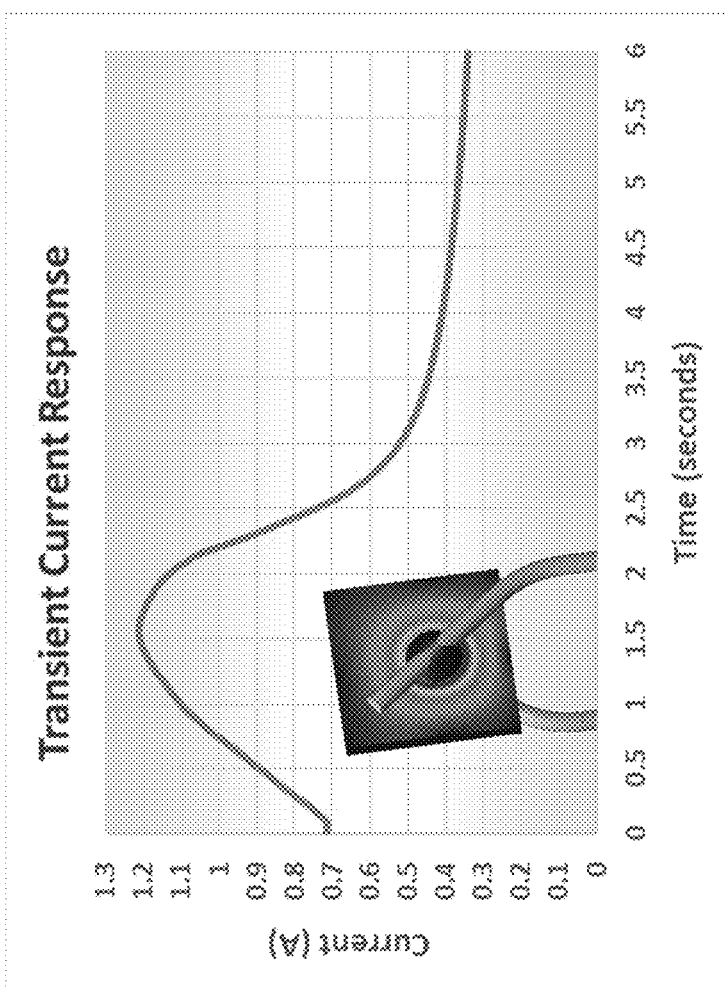
FIG. 12 illustrates a transient current response as a function of time for an example PTCR heater, consistent with implementations of the current subject matter.

FIG. 12 illustrates a transient current response as a function of time of an example heater, consistent with implementations of the current subject matter. In the graph, the current is measured in amps, which increases at a near linear rate, and reaches a peak draw after about 1.5 seconds from activation. Thereafter, the resistance quickly increases to reduce the current draw as the PTCR heater achieves a self-regulating operating temperature.

Although a few variations have been described in detail above, other modifications or additions are possible. For example, the current subject matter can include a vaporizer with PTCR heating element that enables a heat-not-burn (HNB) that may include real tobacco products in order to provide enhanced flavor. In some implementations, the real tobacco products are a solid or semi-solid.

In some implementations, the PTCR heating element includes an aspect ratio of between 1 and 50. For example, the PTCR heating element can include an aspect ratio between 1-5, 5-10, 10-15, 15-20, 20-25, 25-30, 30-35, 35-40, 40-45, or 45-50. Other aspect ratios are possible.

In some implementations, the PTCR heating element includes a composition including constituents such as a mixed-metal oxide; or a composite mixture of two or more mixed-metal oxides; or a composite mixture of one or more mixed-metal oxides with one or more elemental metals, or alternately with one or more binary metal oxides ($MO_x$-type phases), or alternately with one or more binary metal nitrides ($MN_x$-type phases), or alternately with one or more binary metal carbides ($MC_x$-type phases), or alternately with one or more binary metal borides ($MB_x$-type phases), or alternately with one or more binary metal silicides ($MSi_x$-type phases); or a composite mixture of two or more binary metal oxides; or a composite mixture of two or more binary metal oxides with one or more elemental metals, or alternately with one or more binary metal nitrides, or alternately with one or more binary metal carbides, or alternately with one or more binary metal borides, or alternately with one or more binary metal silicides; or a cross-linked polymer composite with one or more elemental metals, or alternately with one or more binary metal oxides, or alternately with one or more binary metal nitrides, or alternately with one or more binary metal carbides, or alternately with one or more binary metal borides, or alternately with one or more binary metal silicides. The composition can include components such as $ABO_3$-type compounds where the identity of A may be, but is not limited to Li, Na, K, Rb, Mg, Ca, Sr, Ba, Y, La, Ce, Pb, Bi, or mixtures thereof, and the identity of B may be, but is not limited to Mg, Al, Sc, Ti, V, Cr, Mn, Fe, Co, Ni, Cu, Zn, Zr, Nb, Hf, Ta, or mixtures thereof; for example, barium titanate ($BaTiO_3$), lead titanate ($PbTiO_3$), lead zirconate ($PbZrO_3$), bismuth aluminate ($BiAlO_3$), alkali niobates ($ANbO_3$, A=Li, Na, K, Rb), alkali tantalates ($ATaO_3$, A=Li, Na, K, Rb), or solid solutions thereof, or solid solutions such as main-group alkali zirconates ($Bi_{0.5}A_{0.5}ZrO_3$, A=Li, Na, K), or solid solutions such as main-group titanate-zirconates ($PbTi_{1-x}Zr_xO_3$), or rare-earth substituted variants such as $Ba_{1-x}RE_xTiO_3$ (RE=La, Ce), among others. Such components are not limited to being explicitly defined by their stoichiometry and therefore may be non-stoichiometric or intergrowth materials. Alternate or additional components can include, for example, compounds such as alkaline earth niobates ($Sr_{1-x}Ba_xNb_2O_6$), Aurivillius-type phases of the general formula $[Bi_2O_2][A_{n-1}BnO_{3n+1}]$, $Bi_4Ti_3O_{12}$, substituted, solid solution, non-stoichiometric, and intergrowth phases thereof. The components may alternately or additionally include elemental metals such as C, Al, Si, Ti, Fe, Zn, Ag, or Bi, among others, binary metal oxides such as MgO, $Al_2O_3$, $SiO_2$, $TiO_2$, $Ti_2O_3$, $Cr_2O_3$, MnO, FeO, CoO, NiO, CuO, ZnO, or $SnO_2$, among others, binary metal nitrides such as TiN, $Mn_3N_2$, $Co_2N$, $Ni_3N$, or $Zn_3N_2$, among others, binary metal carbides such as TiC, among others, binary metal borides such as $ZrB_2$, $NbB_2$, among others, and binary metal silicides such as $NbSi_2$, $WSi_2$, $MoSi_2$, among others. The components may alternately or additionally include polymers such as polyethylene, polyamide, kynar, polytetrafluoroethylene, and combinations thereof among others.

In some implementations, a PTCR heating element is configured to electrically couple to the power source and heat the fluid to form an aerosol, the PTCR heating element including an electrical resistivity that varies based on temperature, the electrical resistivity including a transition zone including an increase in electrical resistivity over a temperature range. In some implementations, the electrical resistivity transition zone begins at a first temperature (e.g., Ti) of between 150° C. and 350° C.; the electrical resistivity transition zone begins at a first temperature of between 200° C. and 300° C.; the electrical resistivity transition zone begins at a first temperature between 220° C. and 290° C.; or the electrical resistivity transition zone begins at a first temperature between 240° C. and 280° C. In some implementations, the increase in the electrical resistivity over the temperature range (e.g., $T_1$ to $T_2$) of the electrical resistivity transition zone includes an increase factor of at least 10 (e.g., the resistivity at $T_2$ is at least 10 times greater than the resistivity at Ti), the increase factor characterizing a relative change in electrical resistivity between electrical resistivity at a first temperature (e.g., Ti) associated with a start of the transition zone and electrical resistivity at a second temperature (e.g., $T_2$) associated with an end of the transition zone. Other factors are possible, for example, the factor can be at least 100, 1000, or greater.

In some implementations, a difference between the start temperature (e.g., Ti) of the transition zone and the end temperature (e.g., $T_2$) of the transition zone can be 500° C. or less. Other temperature ranges are possible, for example, the difference between the start temperature (e.g., Ti) of the transition zone and the end temperature (e.g., $T_2$) of the transition zone can be 200° C. or less, 100° C. or less, 50° C. or less, or smaller.

In some implementations, the electrical resistivity of the PTCR heating element at temperatures below the transition zone (e.g., below $T_1$ is between 2 ohm-cm and 2000 ohm-cm. Other resistivity values are possible, for example, the electrical resistivity of the PTCR heating element at temperatures below the transition zone (e.g., below Ti) can be between 0.2 ohm-cm and 20 ohm-cm, between 2.0 ohm-cm and 20 ohm-cm, between 0.2 ohm-cm and 2.0 ohm-cm, between 2 ohm-cm and 200 ohm-cm, between 20 ohm-cm and 200 ohm-cm, or between 2 ohm-cm and 20 ohm-cm.

The subject matter described herein provides many technical advantages. For example, intrinsic temperature control for a vaporizer is assured in a PTCR heating element at the point of vaporization over a range of applied voltages without the need for temperature sensors or electronic circuitry or microprocessors or algorithms providing means to control power to a PTCR heating element at the point of vaporization. In some implementations, intrinsic temperature control of a PTCR heating element ensures that thermal runaway does not occur under conditions where no vaporizable substance is present, without any additional components such as fuses, sensors, or other shut-off mechanisms that may be required or desired in the absence of temperature control circuitry.

Terminology

The term "vaporizer device" refers to any of a self-contained apparatus, an apparatus that includes two or more separable parts (e.g., a vaporizer body that includes a battery and other hardware, and a cartridge that includes a vaporizable material), and/or the like. Examples of vaporizer devices consistent with implementations of the current subject matter include electronic vaporizers, electronic nicotine delivery systems (ENDS), and/or the like. In general, such vaporizer devices are hand-held devices that heat (e.g., by convection, conduction, radiation, and/or some combination thereof) a vaporizable material to provide an inhalable dose of the material. The vaporizable material used with a vaporizer device may be provided within a cartridge (e.g., a part of the vaporizer that contains the vaporizable material in a reservoir or other container) which may be refillable when empty, or disposable such that a new cartridge containing additional vaporizable material of a same or different type can be used). A vaporizer device may be a cartridge-using vaporizer device, a cartridge-less vaporizer device, or a multi-use vaporizer device capable of use with or without a cartridge. For example, a vaporizer device may include a heating chamber (e.g., an oven or other region in which material is heated by a PTCR heating element) configured to receive a vaporizable material directly into the heating chamber, and/or a reservoir or the like for containing the vaporizable material. In some implementations, a vaporizer device may be configured for use with a liquid vaporizable material (e.g., a carrier solution in which an active and/or inactive ingredient(s) are suspended or held in solution, or a liquid form of the vaporizable material itself), a paste, a wax, and/or a solid vaporizable material. A solid vaporizable material may include a plant material that emits some part of the plant material as the vaporizable material (e.g., such that some part of the plant material remains as waste after the material is vaporized for inhalation by a user) or optionally can be a solid form of the vaporizable material itself, such that all of the solid material may eventually be vaporized for inhalation. A liquid vaporizable material may likewise be capable of being completely vaporized, or may include some portion of the liquid material that remains after all of the material suitable for inhalation has been vaporized. A "vaporizer system," as used herein, may include one or more components, such as a vaporizer device.

As used herein, the terms "wick" or "wicking element" include any material capable of causing fluid motion via capillary pressure.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. An apparatus comprising:
   a reservoir configured to contain a vaporizable material; and
   a PTCR (positive temperature coefficient of resistivity) heating element configured to receive an electrical current flow and heat the vaporizable material to form an aerosol, the PTCR heating element comprising a PTCR material having an electrical resistivity that varies based on temperature, such that when the PTCR heating element is heated above a first temperature, the electrical current flow is reduced to a level that limits further temperature increases of the PTCR heating element;
   wherein the PTCR heating element includes a hole feature extending though the PTCR heating element.

2. The apparatus of claim 1, further comprising an atomizer coupled to the reservoir to receive the vaporizable material, the atomizer including the PTCR heating element.

3. The apparatus of claim 2, wherein the atomizer includes an inlet and an outlet, and the PTCR heating element is arranged between the inlet and the outlet.

4. The apparatus of claim 1, further comprising:
   a cartridge including the reservoir and the PTCR heating element; and
   electrical contacts electrically coupled to the PTCR heating element and configured to provide the electrical current flow to the PTCR heating element from a power source.

5. The apparatus of claim 1, further comprising:
   a pressure sensor; and
   a controller coupled to the pressure sensor and configured to detect inhalation, and in response, electrically connect a power source to the PTCR heating element.

6. The apparatus of claim 1, further comprising a power source configured to provide the electrical current flow.

7. The apparatus of claim 6, further comprising:
   an input configured to electrically connect the power source to the PTCR heating element in response to user input.

8. The apparatus of claim 1, wherein the PTCR heating element includes holes extending therethrough.

9. The apparatus of claim 1, further comprising a wick, wherein the PTCR heating element at least partially surrounds the wick.

10. An apparatus comprising:
a reservoir configured to contain a vaporizable material;
a PTCR (positive temperature coefficient of resistivity) heating element configured to receive an electrical current flow and heat the vaporizable material to form an aerosol, the PTCR heating element comprising a PTCR material having an electrical resistivity, the electrical resistivity including an electrical resistivity transition zone in which the electrical resistivity increases over a temperature range, such that when the PTCR heating element is heated above a first temperature within the transition zone, the electrical current flow is reduced to thereby limit further increases in temperature of the PTCR heating element; and
a wick having an open weave configuration adjacent the PTCR heating element and cylindrical ends, the wick configured to transport the vaporizable material to a location for vaporization, wherein the PTCR heating element is configured to heat the vaporizable material at the location.

11. The apparatus of claim 10, further comprising an atomizer coupled to the reservoir to receive the vaporizable material, the atomizer including the PTCR heating element.

12. The apparatus of claim 11, wherein the atomizer includes an inlet and an outlet, and the PTCR heating element is arranged between the inlet and the outlet.

13. The apparatus of claim 10, further comprising:
a cartridge including the reservoir and the PTCR heating element; and
electrical contacts electrically coupled to the PTCR heating element and configured to provide the electrical current flow to the PTCR heating element from a power source.

14. The apparatus of claim 10, further comprising:
a pressure sensor; and
a controller coupled to the pressure sensor and configured to detect inhalation, and in response, electrically connect a power source to the PTCR heating element.

15. The apparatus of claim 10, further comprising a power source configured to provide the electrical current flow.

16. The apparatus of claim 15, further comprising:
an input configured to electrically connect the power source to the PTCR heating element in response to user input.

17. The apparatus of claim 10, wherein the PTCR heating element is wrapped around at least a portion of the wick.

* * * * *